US010986999B2

(12) United States Patent
Frangioni et al.

(10) Patent No.: US 10,986,999 B2
(45) Date of Patent: Apr. 27, 2021

(54) RANGE-FINDING IN OPTICAL IMAGING

(71) Applicant: CURADEL, LLC, Marlborough, MA (US)

(72) Inventors: John V. Frangioni, Wayland, MA (US); Mark W. Bordo, Worcester, MA (US)

(73) Assignee: Curadel, LLC, Natick, MA (US)

(*) Notice: Subject to any disclaimer, the term of this patent is extended or adjusted under 35 U.S.C. 154(b) by 377 days.

(21) Appl. No.: 15/964,262

(22) Filed: Apr. 27, 2018

(65) Prior Publication Data
US 2018/0310829 A1 Nov. 1, 2018

Related U.S. Application Data

(60) Provisional application No. 62/490,924, filed on Apr. 27, 2017.

(51) Int. Cl.
*A61B 5/00* (2006.01)
*G06T 7/73* (2017.01)
(Continued)

(52) U.S. Cl.
CPC ........ *A61B 5/0077* (2013.01); *A61B 1/00045* (2013.01); *A61B 1/07* (2013.01);
(Continued)

(58) Field of Classification Search
CPC ..... A61B 1/00045; A61B 1/07; A61B 1/3132; A61B 2034/2048; A61B 2034/2057;
(Continued)

(56) References Cited

U.S. PATENT DOCUMENTS

| 5,040,116 A | 8/1991 | Evans, Jr. et al. |
| 7,892,165 B2 | 2/2011 | Nakamura |

(Continued)

FOREIGN PATENT DOCUMENTS

| CN | 106214256 | 12/2016 |
| EP | 1410755 A1 | 4/2004 |
| JP | 2012157383 A | 8/2012 |

OTHER PUBLICATIONS

International Search Report dated Aug. 30, 2018 in connection with PCT/US18/29736.
(Continued)

*Primary Examiner* — Joanne M Hoffman
*Assistant Examiner* — Alexei Bykhovski
(74) *Attorney, Agent, or Firm* — Myers Bigel, P.A.

(57) ABSTRACT

In one embodiment, an imaging system illuminates a surface of tissue with one or more spots of near-infrared (NIR) light within a field of view of a camera of the imaging system. The imaging system captures an image of the one or more spots of NIR light within the field of view of the camera of the imaging system. The imaging system calculates, for each of the one or more spots of NIR light in the captured image, a spot diameter, spot position, or spot shape in the captured image. The imaging system determines a distance between the imaging system and the surface of tissue, based on the calculated spot diameter, spot position, or spot shape of the one or more spots of NIR light in the captured image. The imaging system provides data indicative of the determined distance between the imaging system and the surface of tissue to an electronic display.

23 Claims, 16 Drawing Sheets

(51) Int. Cl.

| | | |
|---|---|---|
| *A61B 1/00* | (2006.01) | |
| *A61B 1/07* | (2006.01) | |
| *G01N 1/28* | (2006.01) | |
| *G01N 33/483* | (2006.01) | |
| *G01N 21/64* | (2006.01) | |
| *G01C 3/08* | (2006.01) | |
| *A61B 34/20* | (2016.01) | |
| *A61B 90/00* | (2016.01) | |
| *A61B 90/30* | (2016.01) | |
| *G01N 1/06* | (2006.01) | |
| *A61B 1/313* | (2006.01) | |
| *A61B 90/20* | (2016.01) | |

(52) U.S. Cl.
CPC .......... *A61B 5/0071* (2013.01); *A61B 5/6886* (2013.01); *A61B 5/7445* (2013.01); *A61B 34/20* (2016.02); *A61B 90/30* (2016.02); *A61B 90/361* (2016.02); *G01C 3/08* (2013.01); *G01N 1/06* (2013.01); *G01N 1/286* (2013.01); *G01N 21/6486* (2013.01); *G01N 33/4833* (2013.01); *G06T 7/74* (2017.01); *A61B 1/3132* (2013.01); *A61B 5/7425* (2013.01); *A61B 90/20* (2016.02); *A61B 2034/2048* (2016.02); *A61B 2034/2057* (2016.02); *A61B 2090/306* (2016.02); *A61B 2090/3614* (2016.02); *A61B 2090/371* (2016.02); *A61B 2560/0233* (2013.01); *G01N 2001/2873* (2013.01); *G06T 2207/10068* (2013.01); *G06T 2207/30244* (2013.01)

(58) Field of Classification Search
CPC ........ A61B 2090/061; A61B 2090/306; A61B 2090/3614; A61B 2090/371; A61B 2560/0233; A61B 34/20; A61B 5/0071; A61B 5/0077; A61B 5/6886; A61B 5/7425; A61B 5/7445; A61B 90/20; A61B 90/30; A61B 90/361; G01C 3/08; G01N 1/06; G01N 1/286; G01N 2001/2873; G01N 21/6486; G01N 33/4833; G06T 2207/10068; G06T 2207/30244; G06T 7/74

See application file for complete search history.

(56) References Cited

U.S. PATENT DOCUMENTS

| | | |
|---|---|---|
| 7,912,532 B2 | 3/2011 | Schmidt et al. |
| 9,360,300 B2 | 6/2016 | DiBernado et al. |
| 9,513,113 B2 | 12/2016 | Yang et al. |
| 2002/0165467 A1 | 11/2002 | Rutenberg |
| 2005/0014995 A1 | 1/2005 | Amundson et al. |
| 2011/0102763 A1 | 5/2011 | Brown et al. |
| 2013/0016185 A1 | 1/2013 | Stolka et al. |
| 2013/0162775 A1 | 6/2013 | Baumann et al. |
| 2013/0162793 A1* | 6/2013 | Dinten ............... G01N 21/6408 348/77 |
| 2015/0018690 A1 | 1/2015 | Kang et al. |
| 2016/0206202 A1* | 7/2016 | Frangioni ............ A61B 5/0084 |
| 2018/0045623 A1* | 2/2018 | Ragan ................. G02B 21/367 |

OTHER PUBLICATIONS

Cai et al. "Tracking multiple surgical instruments in a near-infrared optical system" Taylor & Francis Online; pp. 1-18; May 18, 2016.

Krupa et al. "Autonomous 3-D positioning of surgical instruments in robotized laparoscopic surgery using visual servoing" IEEE Transactions on Robotics and Automation, vol. 19, No. 5; pp. 1-12; Oct. 2003.

Tateishi et al. "A 200Hz small range image sensor using a multi-spot laser projector" pp. 1-6.

Extended European Search Report corresponding to European Patent Application No. 18790421.4 (9 pages) (dated Nov. 9, 2020).

\* cited by examiner

RANGE-FINDING IN OPTICAL IMAGING

RELATED APPLICATION

This application claims priority to U.S. Provisional Patent Appl. No. 62/490,924, filed on Apr. 27, 2017, entitled "RANGE-FINDING IN OPTICAL IMAGING," by John V. Frangioni, the contents of which are incorporated herein by reference.

TECHNICAL FIELD

The present disclosure relates generally to imaging systems and, more particularly, to range-finding in optical imaging.

BACKGROUND

Various forms of imaging systems are used in the healthcare and research fields, today. In some cases, the imaging may be performed in vivo, i.e., within a living organism. Such imaging systems may include, for example, endoscopic imaging systems, laparoscopic imaging systems, open space imaging systems, and the like. In other cases, the imaging may be performed ex vivo, such as in the case of imaging biopsied tissue.

Depending on the use case, images from an imaging system may be on a microscopic or macroscopic scale. For example, lenses may be used in the imaging system to magnify the images that the system captures. In another example, magnification may be achieved during processing of the captured image data. Thus, imaging systems may afford a wide variety of different views to a user.

Typically, the distance between the tip of the imaging system and the imaged subject (e.g., in vivo or ex vivo tissue) is largely unknown. However, the high intensity illumination of many imaging systems can also lead to tissue damage due to heating and burning, if the imaging system is located too close to the subject. For example, in the case of critical surgeries, such as neurosurgery, if the imaging system is too close, it can lead to iatrogenic damage, such as tearing or burning a nerve. In other cases, the distance of an imaging system to a subject, also known as the working distance (WD), needs to be known precisely so that other attributes, such as a horizontal scale bar, can be calculated and displayed.

BRIEF DESCRIPTION OF THE DRAWINGS

The embodiments herein may be better understood by referring to the following description in conjunction with the accompanying drawings in which like reference numerals indicate identically or functionally similar elements, of which.

Figure 1:
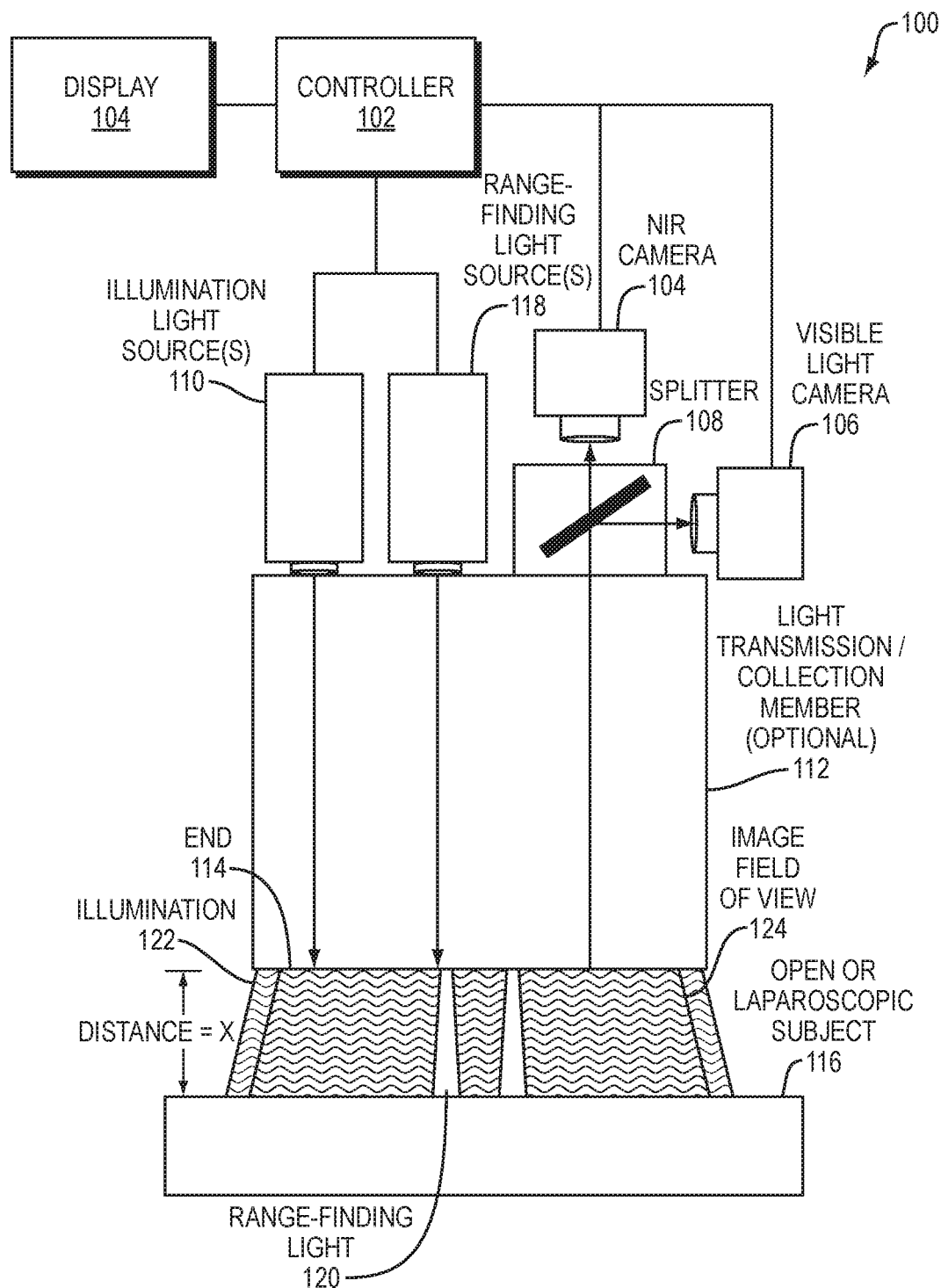
FIG. 1 shows an example embodiment of an imaging system.

In the figures, reference numbers refer to the same or equivalent parts of the present invention throughout the several figures of the drawing.

SUMMARY

According to the techniques described herein, an imaging device images a subject, such as tissue, using both illumination light and range-finding (RF) light. The device may calculate a range between an end of the imaging device and the subject being imaged by assessing one or more attributes of the RF illumination light that appears in the image.

In some embodiments, a method is disclosed that includes illuminating, by an imaging system, a surface of tissue with one or more spots of near-infrared (NIR) light within a field of view of a camera of the imaging system. The method also includes capturing, by the imaging system, an image of the one or more spots of NIR light within the field of view of the camera of the imaging system. The method further includes calculating, by the imaging system and for each of the one or more spots of NIR light in the captured image, a spot diameter, spot position, or spot shape in the captured image. The method also includes determining, by the imaging system, a distance between the imaging system and the surface of tissue, based on the calculated spot diameter, spot position, or spot shape of the one or more spots of NIR light in the captured image. The method further includes providing, by the imaging system, data indicative of the determined distance between the imaging system and the surface of tissue to an electronic display.

In further embodiments, an imaging system is disclosed that includes a near-infrared (NIR) light source, a visible light camera, and an NIR camera. The imaging system also includes a controller coupled to the NIR light source, visible light camera, and NIR camera. The controller includes a processor configured to execute a process and a memory configured to store the process. When executed, the process is configured to illuminate, using the NIR light source, a surface of tissue with one or more spots of NIR light within a field of view of the visible light camera. The process, when executed, is also configured to capture, using the NIR camera, an image of the one or more spots of NIR light within the field of view of the visible light camera. The process, when executed, is additionally configured to calculate, for each of the one or more spots of NIR light in the captured image, a spot diameter, spot position, or spot shape in the captured image. The process, when executed, is also configured to determine a distance between the imaging system and the surface of tissue, based on the calculated spot diameter or spot position of the one or more spots of NIR light in the captured image. The process, when executed, is further configured to provide data indicative of the determined distance between the imaging system and the surface of tissue to an electronic display.

In additional embodiments, a microtome is disclosed. The microtome includes a tissue holder configured to retain a block of tissue. The microtome also includes a blade configured to move across the retained block of tissue to produce a slice of tissue sample from the block of tissue. The microtome further includes an imaging system configured to perform fluorescence imaging on the block of tissue and to perform range-finding on at least one of: the block of tissue, the tissue holder, or the blade.

DETAILED DESCRIPTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

FIG. 1 shows an embodiment of an imaging system that may be used, for example, to image tissue either in vivo or ex vivo. The imaging system 100 may generally include a controller 102, a display 104, a near-infrared (NIR) camera 104, a range-finding light source 118, a visible light camera 106, a splitter mechanism 108, one or more light sources 110, and/or a light transmission/collection member 112. As would be appreciated, imaging system 100 may be adapted for any number of uses including, but not limited to, open surgical imaging, endoscopic or laparoscopic imaging, block face imaging (e.g., of a tissue sample), or the like. Examples of imaging system 100 include the FLARE® (FLuorescence-Assisted Resection and Exploration) imaging systems available from Curadel LLC, Marlborough, Mass., as well as any other type of optical imaging system.

In various embodiments, imaging system 100 may be configured to capture fluorescence images of a subject 116, such as organic tissue, using its cameras 104, 106. Prior to imaging subject 116 and/or during the imaging by imaging system 100, subject 116 may be injected with a fluorescent dye (e.g., a fluorophore) that is optically reactive when exposed to certain wavelengths of light. Generally, subject 116 may be any form of organic tissue in an open or laparoscopic/endoscopic setting, in various embodiments. For example, some dyes may be photo-reactive in the NIR range and emit light when exposed to illumination in this range. Leveraging this, imaging system 100 may capture contrasting images of subject 116 with NIR camera 104 capturing the phosphorescence/NIR images of subject 116 and the dye infused therein, and visible light camera 106 capturing visible light images of subject 116. In general, near-infrared as used herein refers to the range of wavelengths between 660-900 nanometers ("nm").

Generally, and as described in more detail below, controller 102 may provide electronic control over illumination light source(s) 110, one or more range-finding light source(s) 118, and cameras 104, 106, to capture the NIR and visible light images of subject 116, respectively. Controller 102 may also, in some embodiments, combine the imaging data from both types of captured images into a combined image. For example, such a combined image may present the NIR/fluorescence image data as an overlay for the visible image data, thereby providing a visual indication of the locations within subject 116 where the fluorescent dye is located. For example, certain dyes may bind to specific tumors, thereby facilitating visualization of the tumor within subject 116. In another example, such a dye may be injected into the blood stream of a live patient, thereby allowing the user of imaging system 100 to visualize the diffusing of the dye within subject 116. Once the NIR and visible light image data has been processed, controller 102 may provide the processed image data to a local or remote (e.g., connected via a network) display 104 for visualization and review by a user.

In some embodiments, illumination light source(s) 110 may include a visible light source that serves as a light source for visible light camera 106. For example, the visible light source may be, for example, a near-infrared depleted white light source. Notably, this may be a one-hundred and fifty Watt halogen lamp with one or more filters to deplete wavelengths greater than 700 nm. Generally, any light source constrained to wavelengths between 400 nm and 700 nm may operate as the visible light source in light source(s) 110. In further embodiments, however, ambient lighting in the area may be used in part, or in whole, to provide the visible illumination to subject 116.

In some cases, imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field, light source(s) 110 and cameras 104, 106 in an area that is not exposed to broadband light sources. This may be achieved by using an operating room closed to external light sources, or by using a hood or other enclosure or covering for the surgical field that prevents invasion by unwanted spectrum. In other cases, this can be achieved simply by lowering the interfering light sources to a level where the imaging system in minimally affected. The visible light source of illumination light source(s) 110 may then serve as a light source for the visible light camera 106, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

In addition to capturing visible light images of subject 116, NIR camera 104 of imaging system 100 may capture NIR images of subject 116 (and the dye present therein) as illuminated by an excitation NIR light source in illumination light source(s) 110. For example, in certain applications, the excitation light source and resulting emission from the dye present in subject 116 may have wavelengths near or below 700 nm, as with Cy5 dye, which emits light when excited at 650 nm. These near-red dyes may be used with the present system, however, this requires a visible light source that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source should be depleted at the wavelength(s) of interest. As such, the visible light source should more generally be understood to be a source of light that includes some, but not necessarily all, of the wavelengths of visible light.

It should also be understood that, in a far-red imaging system or infrared imaging system such as those noted above, NIR camera 104 described in the example embodiment will instead be a camera sensitive to the emission wavelength of the injected dye or other fluorescent substance, and that other modifications to light sources, filters and other optics will be appropriate. Similar modifications may be made to isolate a band of wavelengths for dye excitation and emission anywhere within or outside the visible light range, provided that suitable optics, cameras, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source and the emission camera, the NIR camera in the example embodiment, for such applications. Cameras sensitive to far-red, near-infrared, and infrared wavelengths are commercially available.

In particular, light source(s) 110 may include an excitation light source that provides light at a wavelength that excites the dye present in subject 116. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by visible light camera 106 (e.g., a video camera, etc.) or the emission wavelength of the dye. The near-infrared band is generally understood to include wavelengths between 700 nm and 1000 nm, and is a useful wavelength range for a number of readily available excitation light sources and dyes that may be used with the systems described herein. Suitable optical coupling and lenses may be provided to direct each of the visible light source and the excitation light source at an area of interest of subject 116.

Generally, splitter 108 may be operable to separate and direct the NIR and visible light received from the illuminated subject 116. For example, splitter 108 may include any number of filters and/or dichroic mirrors, to direct the fluorescence wavelengths towards NIR camera 104 and the visible wavelengths towards visible light camera 106 for capture. A number of arrangements of the cameras 104, 106 and splitter 108 are possible, and may involving reflecting or transmitting either the visible light image or the emission wavelength image.

In various embodiments, imaging system 100 may also include a light transmission/collection member 112 that conveys the light from light source(s) 110, 118 to the surface subject 116 and direct any light (e.g., reflected light, etc.) from subject 116 towards splitter 108 and cameras 104, 106. For example, light transmission/collection member 112 may include any number of fiber optics or other light guides/channels, to direct the illumination from light source(s) 110, 118 towards subject 116 and the captured light from subject 116 towards cameras 104, 106. In further embodiments, light source(s) 110 may be decoupled from light transmission/collection member 112, to provide illumination to subject 116 directly. In some embodiments, light transmission/collection member 112 may also include any number of lenses on its distal end, to transmit light from light source(s) 110, 118 towards subject 116 and collect light from subject 116 for processing by cameras 104, 106.

Typically, the light provided by illumination light source(s) 110 and from range-finding light source(s) 118, which are described in greater detail below, may be transmitted via different channels within light transmission/collection member 112. In other embodiments, they may be mixed, so long as they enter the final lens(es) with different size, position, and/or shape. As shown, so long as the range-finding illumination spot(s) falls within the imaging system field-of-view, and is different from the field-of-view in divergence, position, and/or shape, the techniques herein will work. Note, however, that light transmission/collection member 112 may be optional, in some embodiments. For example, while endoscopic, laparoscopic, etc. application may employ member 112, other implementations, such as open surgical, may not require member 112 and this component can be omitted.

NIR camera 104 may be any still or moving image camera suitable for capturing images at the emission wavelength of the excited dye present in subject 116. The near-infrared camera may be, for example, an Orca-ER near-infrared camera with settings of gain 7, 2×2 binning, 640×480 pixel field of view, and an exposure time of 20 msec and an effective frame rate of fifteen frames per second. The Orca-ER is commercially available from Hamamatsu Photonic Systems of Bridgewater, N.J. It will be understood that the NIR camera 104 in FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term "emission wavelength camera" is intended to refer to any such camera that may be used with the systems described herein.

Visible light camera 106 may be any video camera suitable for capturing images of the surgical field 106 in the visible light spectrum. In further embodiments, the visible light camera 106 may instead be a camera configured to take still images, as opposed to video. In one embodiment, camera 106 is a color video camera model HV-D27, commercially available from Hitachi of Tarrytown, N.Y. For example, the video camera 106 may capture red-green-blue (RGB) images at thirty frames per second at a resolution of 640×480 pixels, or at any other number of frames or resolutions, as desired. In another example, camera 106 may be a high resolution Canon EOS 700 white light camera available from Canon, Melville, N.Y., although any other suitable white light camera can be used in other implementations. More generally, NIR camera 104 and visible light camera 106 may be any device capable of photonic detection and conversion to electronic images, including linear photodiode arrays, charge coupled device arrays, scanning photomultiplier tubes, and so forth.

Display 104 may be a television, high-definition television, computer monitor, or other display configured to receive and render signals from controller 102. In some embodiments, display 104 may be a monocular or binocular eyepiece of the surgical microscope, with the near-infrared image superimposed on the visible light image in the eyepiece. In another embodiment, the eyepiece may use direct optical coupling of the surgical field to the eyepiece for conventional microscopic viewing, with the near-infrared image projected onto the eyepiece using, for example, heads-up display technology.

Generally, the controller 102 should be capable of digital filtering, gain adjustment, color balancing, and/or any other conventional image processing functions. The image from the NIR camera 104 is also typically shifted into the visible light range for display at some prominent wavelength, e.g., a color distinct from the visible light colors of the captured and/or displayed image data from camera 106, so that a superimposed image will clearly depict the dye. The controller 102 may also perform image processing to combine the image from the NIR camera 104 and the visible light camera 106. Where the images are displayed side-by-side, this may simply entail rendering the images in suitable locations on a computer screen. Where the images are superimposed, a frame rate adjustment may be required. That is, if the visible light camera 106 is capturing images at the conventional rate of thirty frames per second and the NIR camera 104 is taking still pictures with an effective frame rate of fifteen frames per second, some additional processing may be required to render the superimposed images concurrently. This may entail either reducing the frame rate of the visible light camera 106 to the frame rate of the NIR camera 104 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

In one embodiment, the visible light source of light source(s) 110 is a near-infrared depleted visible light source, the excitation light source is a 760 nm, 2.5 W laser diode, the dye is indocyanine green or ZW800-1, and imaging system 100 includes a 780 nm dichroic mirror configured to transmit near-infrared light and reflect visible light, the a 781 nm longpass emission filter, and a 400 nm to 700 nm filter. The controller 102 comprises a processing circuit configured with software for image capture from the NIR camera 104 and the visible light camera 106, for making suitable color adjustment to the images from the NIR camera 104, for making frame rate adjustments to the visible light camera 106 image, and for combining the two images for superimposed display on the display 104.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

In further embodiments, imaging system 100 may be adapted for use in an endoscope or laparoscope. Typically, a laparoscope is inserted into a body cavity through an incision, as distinguished from an endo scope that is inserted through an existing body opening such as the throat or rectum. A laparoscope has a different form factor than an endoscope, including different dimensional requirements. Furthermore, use of a laparoscope involves at least one additional step of making an incision into a body so that the laparoscope may be inserted into a body cavity. It will further be appreciated that the imaging system 100 may be used to simplify imaging devices other than endoscopes and laparoscopes, such as by providing an integrated, coaxial illumination and image capture device using the techniques described above.

Figure 2:
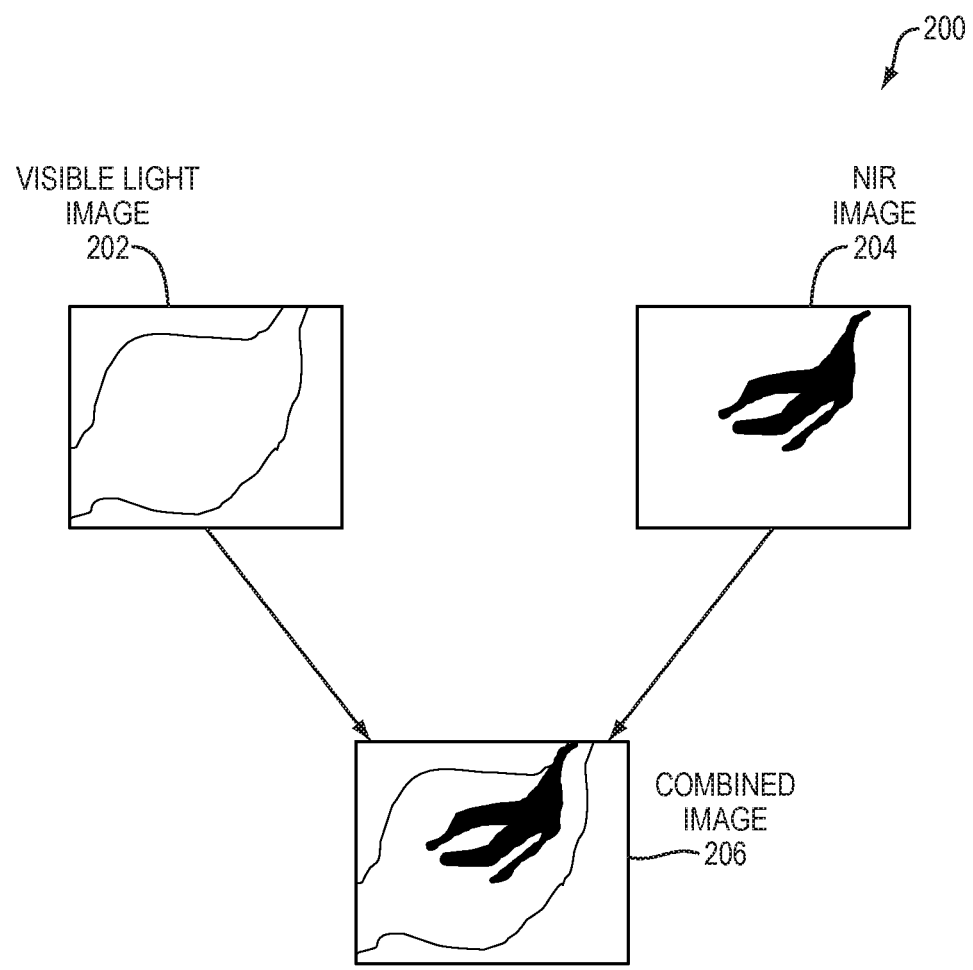
FIG. 2 shows the combination of visible and fluorescence images.

FIG. 2 shows an image displaying both a circulatory system and surrounding tissue. As described above, a visible light tissue image 202 is captured of tissue within a surgical field. As noted above, the visible light tissue image 202 may include a subset of visible light wavelengths when an optical channel for dye imaging includes a wavelength within the visible light range. A near-infrared image 204 is also captured of the same (or an overlapping) field of view of the surgical field. Although referred to here for convenience as a near-infrared image, it should be clear that the dye-based image 204 may also, or instead, employ other wavelengths, such as far-red or infrared wavelengths. The near-infrared image 204 may be shifted to a visible wavelength for display, preferably using a color that is prominent when superimposed on the visible light tissue image 202. The images 402, 404 may be frame-rate adjusted as appropriate for video display of the surgical field.

The images may be displayed separately as the visible light tissue image 202 and the near-infrared image 204. Or the images 202, 204 may be combined into a combined image 206 by the image processing unit described above. The combined image 206 may then be used as an aid to the procedures described above, or to any other surgical or diagnostic procedure that might benefit from the dye-based imaging techniques described herein.

As noted above, the distance between the end of an optical imaging system and a subject are typically unknown. At too great of a distance, the imaging system may be unable to accurately captured the needed image information from the subject. Conversely, at too close of a distance, the imaging system may inadvertently damage and/or burn the subject, due to physical contact and/or the high intensity of the illumination. For example, referring again briefly to FIG. 1, assume that end 114 of imaging system 100 is located at a distance=X from the surface of subject 116. At a given threshold distance=t, the illumination 122 from illumination light source(s) 110 may cause damage to subject 116. Thus, if X≤t, imaging device 100 may damage subject 116. As would be appreciated, the threshold distance may also be a function of the subject type and/or the exposure time to the illumination from light source(s) 110. However, the actual distance X from subject 116 is often unknown.

As described in greater detail below, imaging system 100 may also be operable to determine the range/distance between end 114 of imaging system 100 (e.g., a tip of light transmission/collection member 112). Notably, during use, range-finding light source(s) 118 may transmit range-finding light 126 onto subject 116 while illumination light source(s) 110 transmit illumination 122 onto subject 116. As shown, illumination 122 and range finding light 126 may overlap on the surface of subject 116. Thus, the images captured by cameras 104, 106 within field of view 124 may include both areas of subject 116 that are illuminated by only illumination 122 and those areas of subject 116 that are also illuminated by range-finding light 126. In turn, controller 102 may assess the different types of illumination present in the image data, to determine the distance between end 114 and subject 116.

Figure 3:
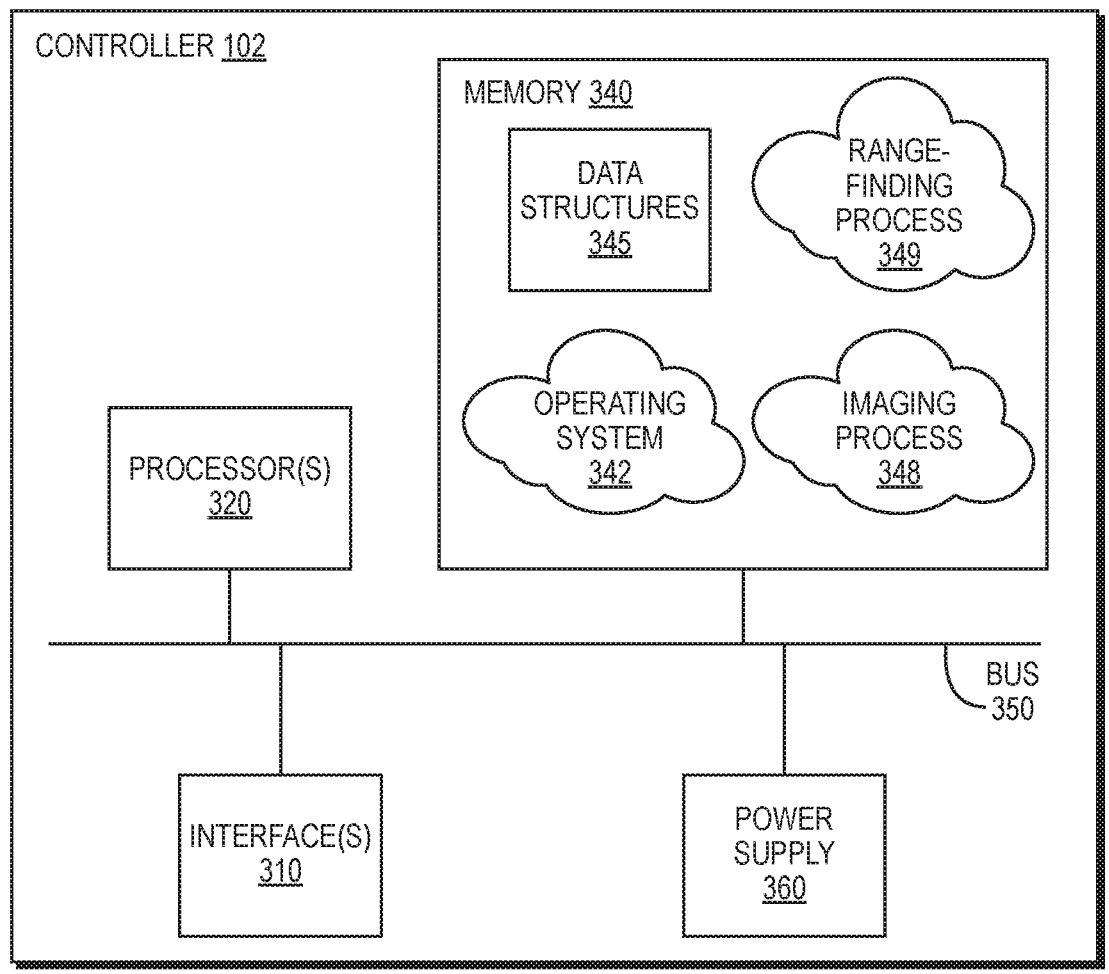
FIG. 3 illustrates an example controller for an imaging system.

FIG. 3 illustrates a controller 102 that may be used as part of any of the imaging systems/devices described herein, according to various embodiments. As shown, controller 102 may comprise one or more network interfaces 310 (e.g., wired, wireless, etc.), at least one processor 320, and a memory 340 interconnected by a system bus 350, as well as a power supply 360 that provides electrical power to controller 102.

The interface(s) 310 contain the mechanical, electrical, and signaling circuitry for communicating data with other components of the imaging device/system and/or with other computing devices (e.g., via a computer network). For example, interface(s) 310 may be configured to transmit and/or receive data using a variety of different communication protocols via a communication network (e.g., to upload image data to a cloud service, to download software or data updates, etc.). In further examples, interface(s) 310 may be coupled to the various components of the imaging device to provide control commands to the camera(s), lighting source(s), etc., of the imaging device and/or to receive captured image data from the camera(s). Interface(s) 310 may also be in communication with an electronic display to display the resulting images after processing.

The memory 340 comprises a plurality of storage locations that are addressable by the processor 320 and the network interfaces 310 for storing software programs and data structures associated with the embodiments described herein. The processor 320 may comprise hardware elements or hardware logic adapted to execute the software programs and manipulate the data structures 345. An operating system 342, portions of which are typically resident in memory 340 and executed by the processor 320, functionally organizes the device by, inter alia, invoking operations in support of software processes and/or services executing on the device. These software processes and/or services may comprise an imaging process 348 and, illustratively, a range-finding process 349, as described herein.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, where certain processes have been shown separately, those skilled in the art will appreciate that processes may be routines or modules within other processes.

Imaging process 348, when executed by processor(s) 320, may be operable to perform any of the imaging functions described herein. For example, imaging process 348 may provide control over the components of the imaging device, to capture both color and fluorescence image data regarding organic tissue of interest. In turn, imaging process 348 may process the captured image data to form display data for display by an electronic display. For example, imaging process 348 may combine both the color and fluorescence data into an overlay image for display by the electronic display. Such a displayed image may be fully in color or at least partially in black and white or grayscale, in various embodiments.

According to various embodiments, range-finding process 349 may operate in conjunction with imaging process 348 to determine the distance/range between an end of the imaging system and the subject being imaged, also known as the working distance (WD). Notably, range-finding process 349 may provide control instructions to the light source(s) of the imaging system and/or to the cameras of the system, to obtain images of the subject (e.g., in vivo or ex vivo tissue). In turn, range-finding process 349 may analyze the captured image data, to determine the range/distance between the end of the imaging system and the subject. Knowing the WD will often enable calculation or estimation of other imaging system attributes, such as a horizontal scale bar, system resolution, illumination intensity level, etc. It also permits other procedures, such as biopsy, resection, lavage, or injection to be performed with a higher safety factor, especially if the working channel through which the procedure is carried out is contained within the endoscope/laparoscope equipped with range-finding.

Figure 4A:
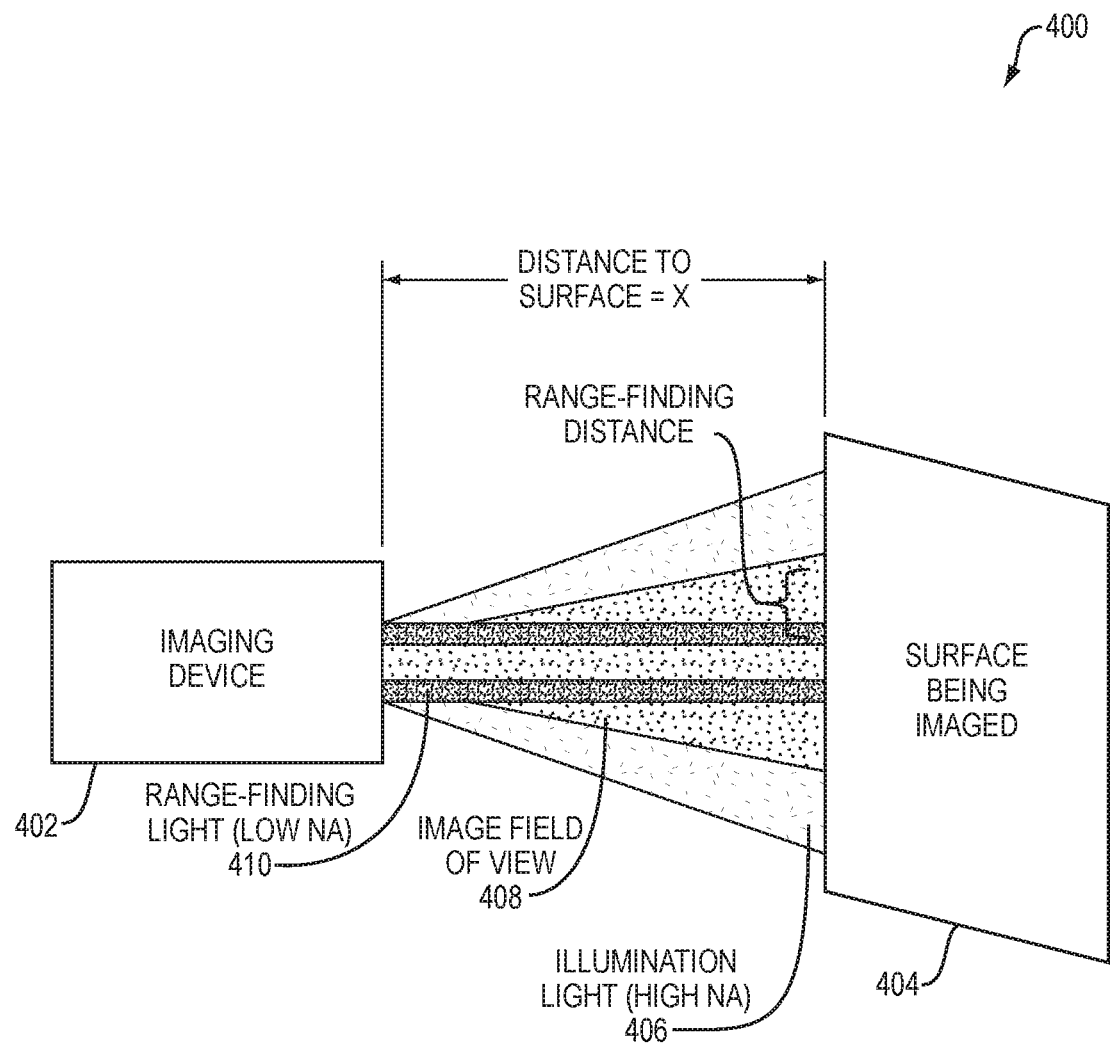
FIGS. 4A-4B illustrate examples of range-finding in an optical imaging system.
Figure 4B:
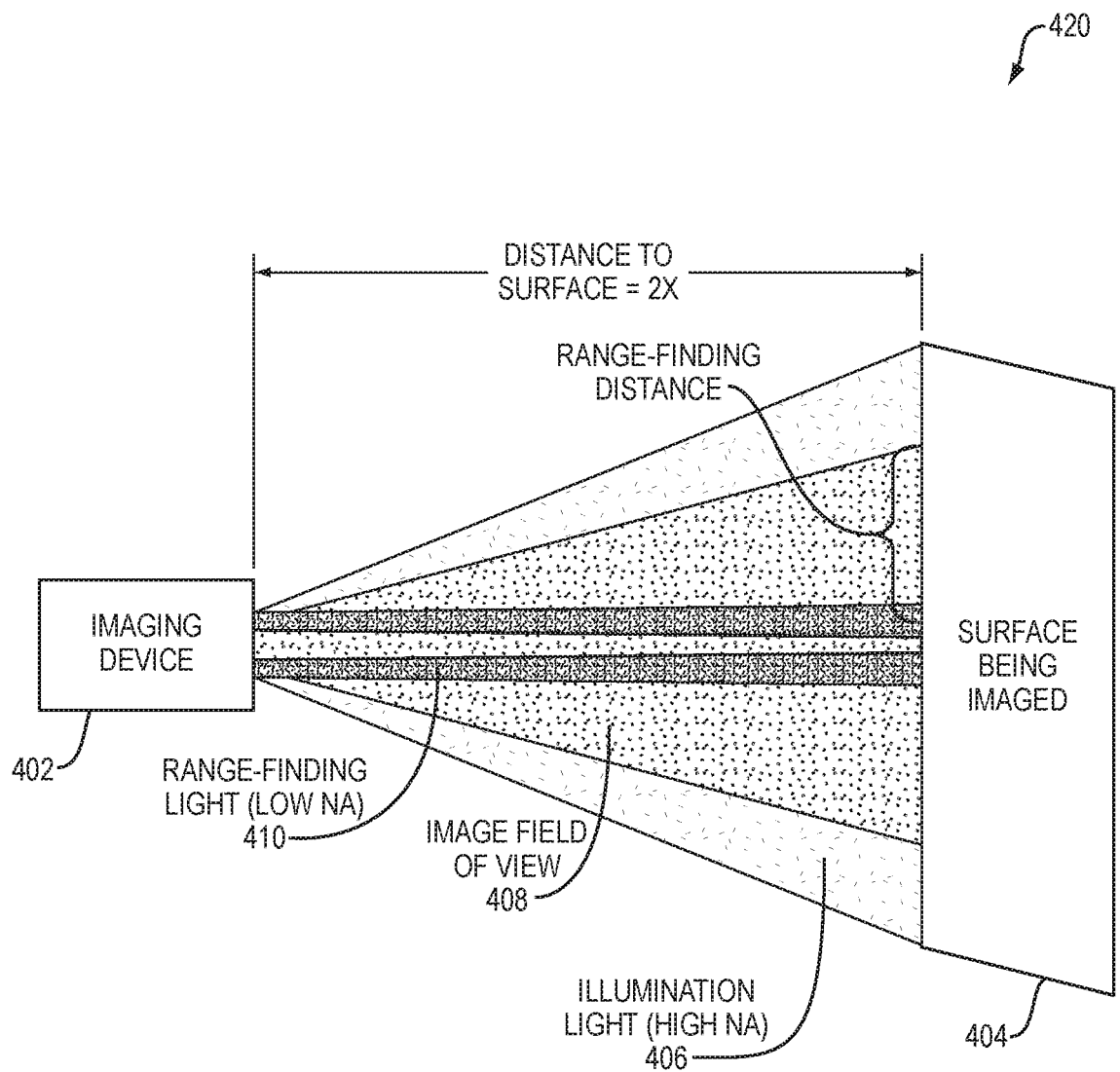

FIGS. 4A-4B illustrate examples of range-finding in an optical imaging system, according to various embodiments. As shown, range-finding process 349 may leverage the differential divergence of light, range-finding spot position within the image, and/or spot shape, to determine the precise distance from an end of the imaging system to the surface of the imaged subject. As would be appreciated, all optical imaging systems require uniform illumination of the surface being imaged. In general, this is achieved using high numerical aperture (NA) fibers or lenses, so that the cone of illumination light 406 is always larger than the object or area being imaged. This results in homogeneous illumination levels without edge effects.

According to various embodiments, the techniques described herein may use invisible, near-infrared (e.g., illumination and imaging in the 660-900 nm range), to provide range-finding capabilities to visible and/or NIR imaging systems, such as imaging device 402 shown. As would be appreciated, imaging device 402 may include any or all of the components described previously with respect to imaging system 100 and, in particular, execute range-finding process 349 to perform the functions described herein.

As shown in FIG. 4A, imaging device 402 may use a wavelength or wavelengths that is detectable to the imaging system, but is otherwise not visible and/or hidden from the user, to illuminate one or more small spots of NIR light on the surface 404 being imaged. In other words, the imaging device 402 may be configured to emit a range-finding light 410 onto the surface 404 and capture images of the illuminated surface 404. In some embodiments, imaging device 402 may use small diameter optical fibers or lenses, to produce the range-finding spots on surface 404. These range-finding spots, as they will now be referred to, or at least portions of each spot, are adjusted to fall within the field-of-view at all distances desired to be measured.

In various embodiments, when using range-finding light with a NIR fluorescence imaging system, a wavelength may be selected that falls within the emission band detected by the imaging system. Normally, the NIR excitation light is chosen to be far outside the emission band so that you have a black background. However, for range-finding, the NIR fluorescence channel may be used to detect the range-finding light, so it needs to fall within the detected emission wavelengths. For example, using a Lab-FLARE® imaging system by Curadel LLC, Marlborough, Mass., one might choose to use 730 nm for range-finding detection on Channel #1 (685-735 nm emission band) or 808 nm for range-finding detection on Channel #2 (>781 nm emission band).

As the optical imaging device is moved towards and away from a surface, the relationship of these spots to the edge of the field of view, and to a lesser extent to each other, will change dramatically. To demonstrate this point, FIGS. 4A-4B each illustrate imaging device 402 when located at different distances to surface 404. Notably, FIG. 4A illustrates the case in which this distance is X and FIG. 4B illustrates the case in which this distance is increased to 2× (i.e., double the distance in FIG. 4A).

In various embodiments, range-finding process 349 may assess captured image data from surface 404, to identify the center (i.e., position within the FOV) of each spot (e.g., the center point of a circle or ellipse of light), the diameter of each spot, and/or the shape of each spot formed by range-finding light 410 on surface 404. In turn, range-finding process 349 may use this information to determine to determine the "range-finding distance." As noted, illumination light 406, which may be provided by high NA fibers or lenses, may be configured to provide illumination to an area larger than that of the captured image field of view 408.

Provided that imaging device 402 was calibrated properly at the factory or prior to imaging, the range-finding distance will provide the exact distance of the device to object distance. Although the "range-finding distance" can be calculated using only a single range-finding spot, the preferred embodiment, other embodiments use two or more spots. For example, using four range-finding spots offers additional accuracy, in the setting of uneven surfaces. That is, the center point to edge of field-of-view distance provides the distance of that particular spot to that particular area of the object being imaged. Generally, the more spots that are used, the higher the topographic variations that can be measured. As a tradeoff, however, more spots increases the computation time, also slowing down the calculations. In various cases, a range-finding spot might appear as an oval (ellipse) or even more complex shape due to topographic variation of the object being imaged. Regardless of the shape of the spot, range-finding process 349 may identify the geometric center of the resulting shape for purposes of determining the distance to the imaged surface. While a circular range-finding spot (when projected onto a flat surface) is preferred, other projected shapes can also be used with the techniques herein, as desired (e.g., by projecting a triangle, square or other quadrilateral, etc.). Again, the more range-finding spots used, the more discriminating the power of the distance in the case of complex shapes.

Range-finding process 349 can assign "relative" distances without calibration. However, in order to assign absolute distance from imaging device 402 to surface 404, the system must be calibrated. If the range-finding spots are mechanically fixed in relationship to the imaging lens, as they would be under most circumstances, this calibration should only have to occur once at the factory. However, in-field performance verification can be performed at any time by setting a known distance from imaging device 402 to a surface and measuring the "range-finding distance." This particular range-finding distance would be assigned to the imaging device to object distance in a lookup table (e.g., in data structures 345) and used by range-finding process 349.

Note that the range-finding spot(s) must typically be different in rate of divergence, size, and/or shape compared to the camera field-of-view, and must also fall within the camera field-of-view at all desired distances. The accuracy of the range-finding system is a complex function of the starting spot size, as well as the angles and locations relative to the camera field-of-view lens.

Figure 5A:
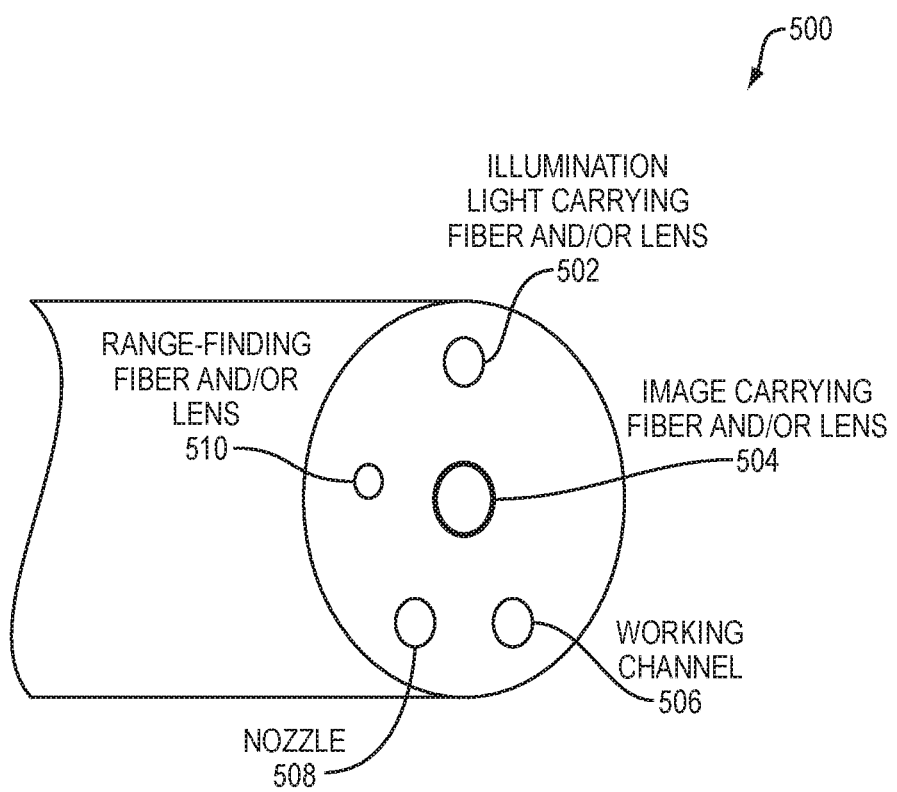
FIGS. 5A-5E illustrate examples of range-finding from the end of a scope.

FIGS. 5A-5E illustrate examples of range-finding from the end of a scope, in various embodiments. An example scope 500 is shown in FIG. 5A. In general, the techniques described herein can be applied to any form of scope used for medical applications, such as endoscopy, laparoscopy, thoracoscopy, or the like. As shown, the end of scope 500 may include any number of illumination light carrying fibers and lenses 502 via which NIR and visible light are transmitted towards the surface of the subject to be imaged. Likewise, the end of scope 500 may include any number of range-finding fibers and lenses 510 that convey the range-finding light towards the surface of the subject.

In addition, scope 500 may include any number of image carrying fibers and lenses 504 configured to receive light from the imaged surface and provide the captured light to the cameras of the imaging system. As would be appreciated, fibers and lenses 502-504, and 510 may be located at any desired location along the surface of the shown end of scope 500 and may, in some embodiments, be separated by use type (e.g., NIR, visible light, etc.) or combined into a single light transmission/collection member 512. Scope 500 may also include various other features, such as a working channel 506 and/or a nozzle 508 (e.g., an air nozzle, a water nozzle, etc.) that can be actuated during use to provide water, air, or other substance to the imaged surface. By leveraging the range-finding techniques herein, procedures such as biopsy, resection, lavage, injection, etc., can be performed via working channel 506 with a higher safety factor because the absolute position of the end of the scope relative to the tissue would be available to the user.

In various embodiments, the distance between the shown end of scope 500 and that of an imaged surface may be determined using the above approach by emitting one or more range-finding beams of light from range-finding light carrying fibers and/or lenses 510 towards the imaged surface, while illumination light carrying fibers and/or lenses 502 emit illumination light onto the surface so that the surface can be seen during imaging. In turn, image carrying fibers and/or lenses 504 may provide the captured image information to the NIR and/or visible light cameras of the system, which can be analyzed to determine the distance to the surface by comparing the locations of the range-finding spot(s) on the surface to the edge(s) of the captured image(s). In some embodiments, illumination light carrying fiber and lenses 502 may be much higher NA than that of the range-finding light fibers and lenses 510 that emit the range-finding beam(s) onto the surface. In various embodiments, the terminal lenses of the fibers shown may also be optional.

As would be appreciated, the techniques herein can also be used to enhance surgical navigation mechanisms that may be in use. For example, the linear distance from the tip of scope 500 to the tissue surface computed using the techniques herein can be combined with other sensor data, such as accelerometer and/or gyroscopic data, to permit very precise surgical navigation of scope 500 in three dimensions. Notably, in many types of surgery, especially minimally-invasive and robotic surgery, the precise location of an instrument is of paramount importance. Range-finding, as described in this application permits precise and accurate measurement of linear distance from the tip of an endoscope/laparoscope or other imaging device, and the tissue of interest. By combining this absolute linear distance measurement with additional data sets, it should be possible to locate the imaging device in a three dimensional space.

By way of example of surgical navigation, a gyroscope, which is currently available as a small integrated circuit using MEMS technology, can provide pitch, roll, and azimuthal angle, i.e., the rotation vector for orientation. An accelerometer can also provide linear acceleration in three dimensions (x, y, and z). Some recent products, in fact, combine a gyroscope, accelerometer, and even a magnetometer into a single small integrated circuit, thus providing 6- or 9-axis relative coordinates. By combining just the rotation vector and linear acceleration (6-axis), though, it is possible to locate an object in relative terms in 3D space. However, in order to orient and scale the position in absolute terms, the linear distance from range-finding is required. That is, the absolute linear distance provides a calibration factor for the rotational and linear axes, such that a precise, three-dimensional position of the imaging device and/or procedural instrument can then be derived. This absolute calibration using range-finding distance can be similarly applied to 9-axis relative coordinate data.

Figure 5B:
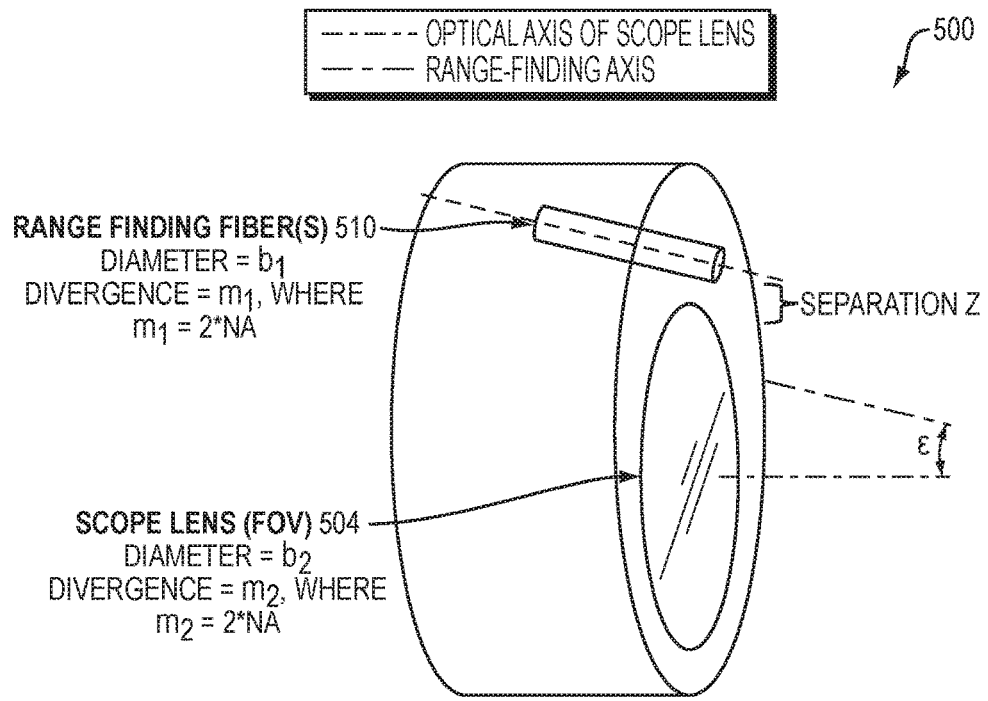
Figure 5C:
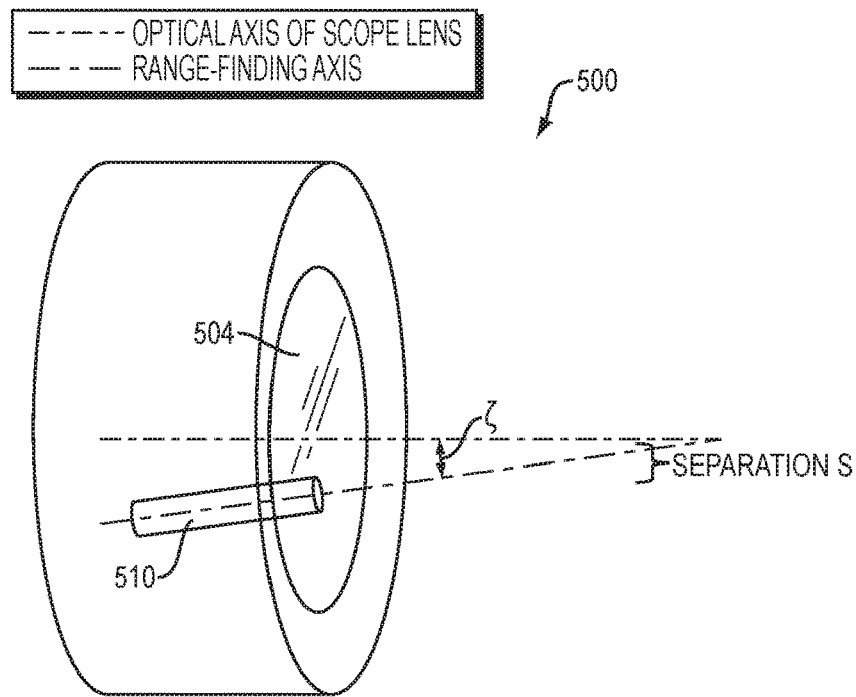

FIGS. 5B-5C respectively illustrate side and top views of scope 500 in greater detail. As shown, let "field of view" (FOV) refer to the camera field of view of the subject tissue that is provided by the image carrying fiber and lens 504. Typically, this FOV is square, with an equal number of pixels in both the horizontal and vertical axis of the captured image. Also, let the "optical axis" refer to the center axis of the camera's FOV. Similarly, let the "range-finding axis" refer to the center axis of the range-finding illumination provided by range-finding fiber and lens 510.

In its simplest form, the range-finding techniques introduced herein require only the addition of a single optical fiber to a standard scope that has a main objective lens. In further embodiments, however, a second range-finding fiber can be added, to employ two independent range-finding wavelengths, as detailed below.

For illustrative purposes, assume that the one or more range-finding fiber(s) 510 has a diameter $b_1$ and a divergence of its beam determined by its NA. Similarly, let the lens 504 for the camera have a diameter $b_2$. Mathematically, the slope of the change of the spot diameter of the range-finding illumination over an object distance X, is given by the slope $m_1=2*NA$. Similarly, the divergence for the image carrying lens 504 may be $m_2=2*NA$. Fiber 510 is separated from the main objective lens 504 of the scope by a distance z as well as a distance s, and is also angularly offset in two axes relative to the optical axis by the angles Epsilon and Zeta shown. As explained below, these angular offsets are extremely important because Epsilon determines the sensitivity to large object distances and Zeta determines the left/right position of the spot at large distances. The separation s determines the position of the spot at X=0.

Figure 5D:
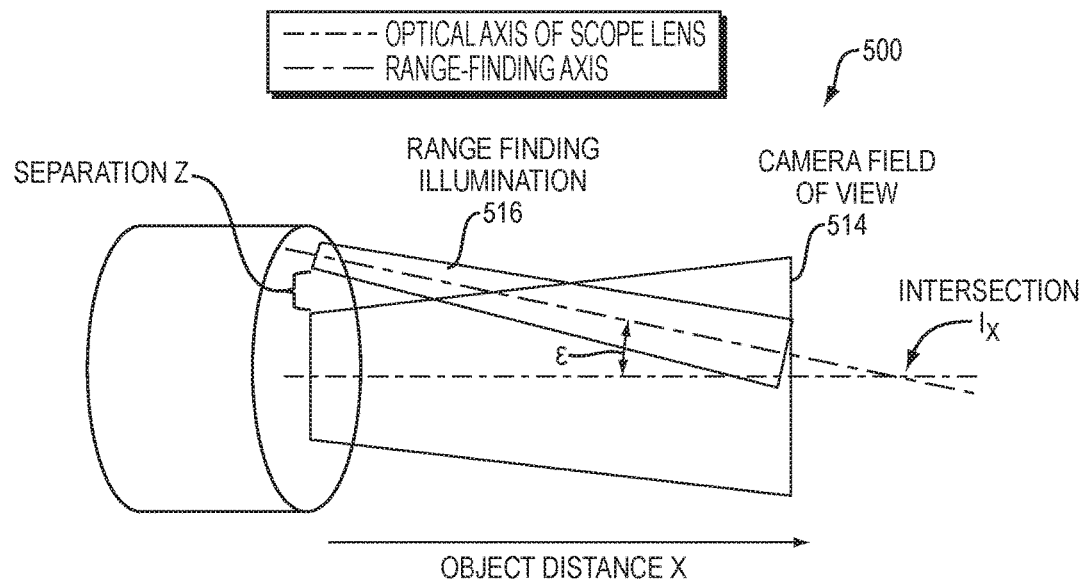
Figure 5E:
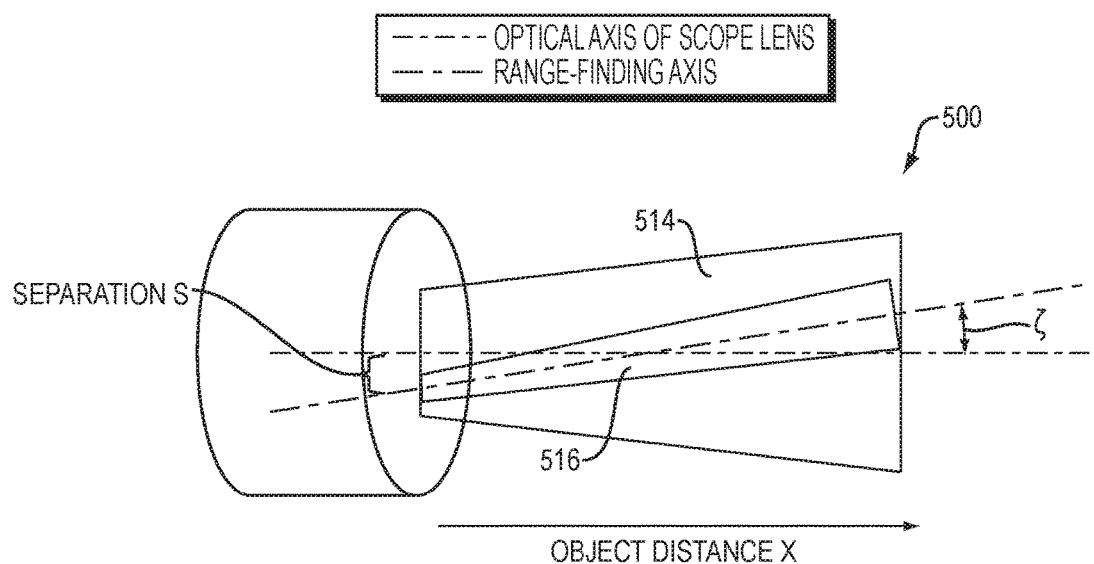

FIGS. 5D-5E illustrate side and top views of scope 500 during range-finding. More specifically, FIGS. 5D-5E illustrate the divergence of the spot formed by range-finding illumination 516 (e.g., from a fiber 510) relative to the camera FOV 514 (i.e., optical axis of the scope lens 504). Importantly, the angle Epsilon may be selected such that the intersection of the range-finding axis with the optical axis occurs at a particular distance $I_x$. $I_x$, in turn, determines sensitivity to far distances, much like the sight of a firearm.

Figure 6A:
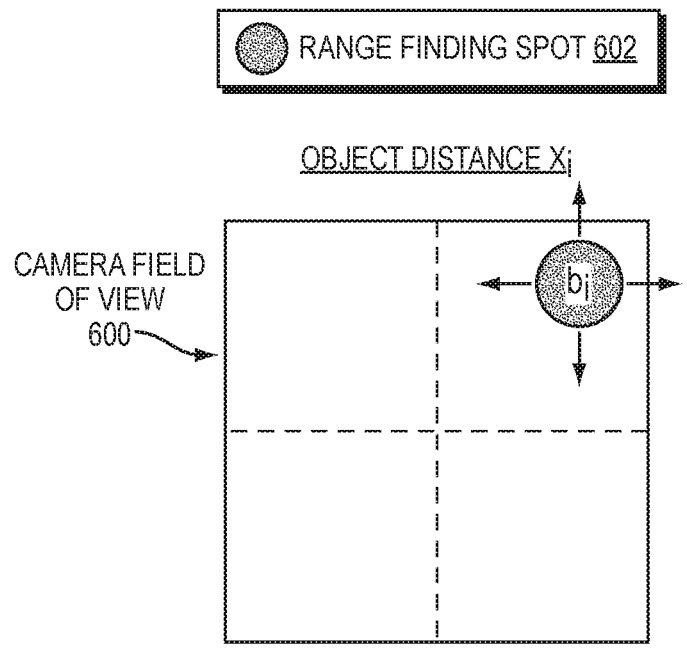
FIGS. 6A-6E illustrate examples of using range-finding spots to determine distance.
Figure 6B:
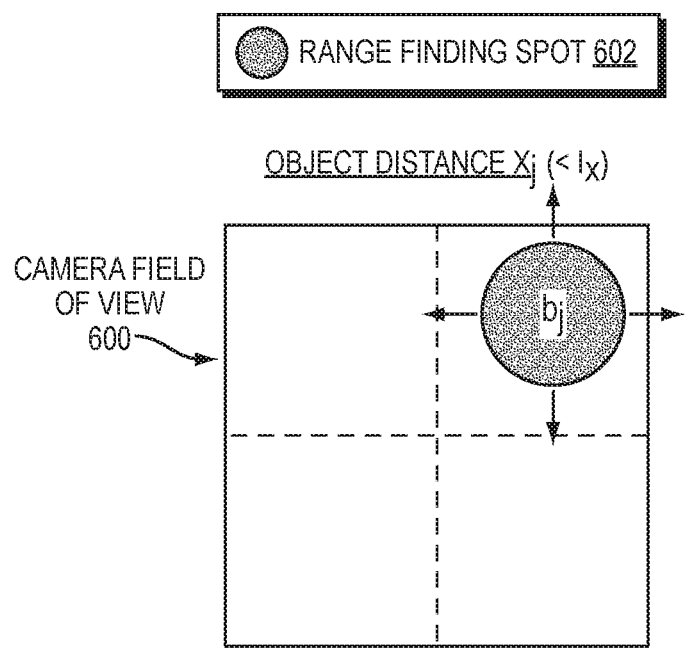

FIGS. 6A-6E illustrate examples of using range-finding spots to determine distance, in various embodiments. Continuing the examples of FIGS. 5A-5E, the relationships among separation distances z and s, angles Epsilon and Zeta, diameters $b_1$ and $b_2$, and slopes (i.e., divergences) $m_1$ and $m_2$ are complex. In particular, at short distances, say 0-5 centimeters (cm), the main change of the range-finding spot will be in diameter b, as shown in FIGS. 6A-6B. More specifically, assume that the range-finding illumination results in a range-finding spot 602 within the camera field of view 600. As shown in FIG. 6A, assume that the imaging system is at an object distance $X_i$, resulting in range-finding spot 602 having a diameter of $b_i$. However, as shown in FIG. 6B, when the imaging system is moved to a farther distance of $X_j$, where $X_j < I_x$, the diameter of range-finding spot 602 increases to a diameter of $b_j$.

Figure 6C:
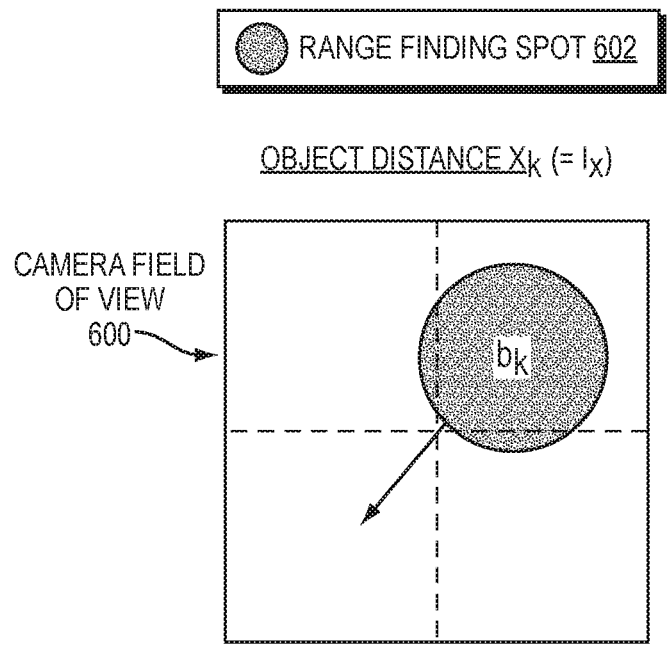
Figure 6D:
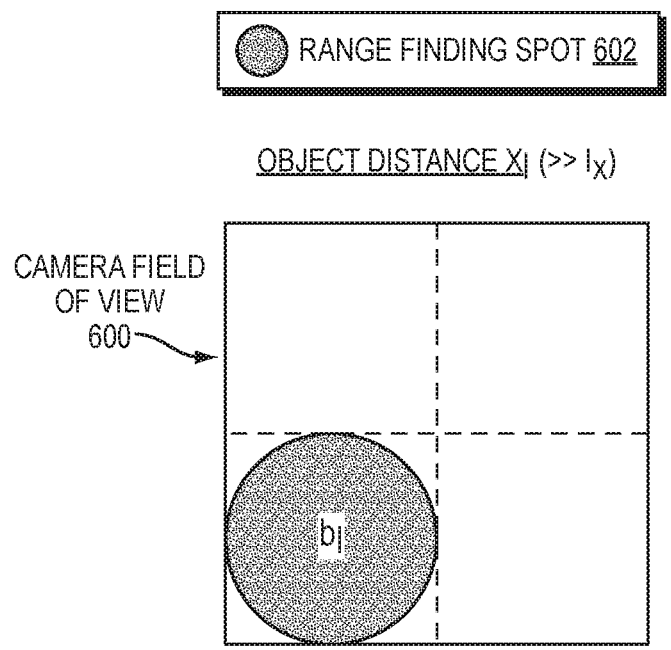

FIGS. 6C-6D illustrate examples of the movement of range-finding spot 602 within camera field of view 600. Notably, the separations z and s, and angles Epsilon and Zeta, also force simultaneous horizontal and vertical movements of range-finding spot 602 within camera field of view 600. More specifically, at object distance $X_k$, with $X_k=I_x$, range-finding spot 602 may be located in the right upper quadrant of camera field of view 600 with a diameter of $b_k$, as shown in FIG. 6C. However, in FIG. 6D, range-finding spot 602 may be located in the lower left quadrant of field of view 600 with a diameter of $b_1$, at object distance $X_1 \gg I_x$. Epsilon will therefore be chosen carefully to give maximal change at long distances, say 5-10 cm. A diagonal movement of range-finding spot 602 is also preferable to a simple up/down movement, so that the number of available pixels is maximized. By exploiting diagonal movement, we gain the square root of 2=1.41-fold more pixels, which translates to higher precision in the measurements.

Mathematically, the sizes of range-finding spot 602 and camera field of view 600 can be described by the following algebraic equations, in various embodiments:

$$\text{spot size} = m_1 * X + b \quad \text{(Equation 1)}$$

where $m_1$=slope of spot divergence=$2*NA$ and $b_1$=fiber diameter for the range-finding illumination, as shown in FIGS. 5B-5C. Similarly, the camera FOV can be calculated as follows:

$$\text{camera FOV} = m_2 * X + b_2 \quad \text{(Equation 2)}$$

where $m_2$=slope of lens divergence=$2*NA$ and $b_2$=objective lens diameter.

Thus, the ratio of the range-finding spot size to the camera FOV, which changes non-linearly as a function of object distance X, is given by:

$$\frac{m_1 * X + b_1}{m_2 * X + b_2} \quad \text{(Equation 3)}$$

Some of the variables above are highly constrained. For example, in a 6 mm OD scope, the largest possible size of the objective lens will be approximately 2.5 mm, giving $b_2=0.25$ cm. The divergence of the field-of-view (conceptually equivalent to the NA of illumination light) is 0.7 in most scopes used in the industry, giving $m_2=1.4$. However, a lower divergence can also be used, if desired.

Prototyping was performed to verify the techniques herein by first evaluating three conventional 10 mm diameter laparoscopes with and without a camera coupler, to confirm that the "typical" FOV divergence (i.e., NA) of a laparoscope is ≈0.7. When the camera coupler was in place, each scope was tested across the range from fully zoomed in to fully zoomed out. Each scope was also tested without the camera attached (e.g., by looking through the eyepiece). As shown in Table 1 below, using the eyepiece only results in slopes of 1.38 to 1.42, corresponding to NA values of 0.69-0.71, which confirms the belief that 10 mm laparoscopes are designed for NA 0.7. Note that the addition of the camera coupler and zooming all the way in reduces NA, and hence light gathering, significantly. Thus, it is a significant advantage to be able to choose a desired NA when constructing a scope in accordance with the teachings herein.

TABLE 1

| Scope | Condition | Slope | Offset | R2 |
|---|---|---|---|---|
| Unnamed 30 Degree Scope | Zoomed In | 0.64171662 | 0.456511591 | 0.999980156 |
| Unnamed 30 Degree Scope | Zoomed Out | 1.660272061 | −0.669445413 | 0.987861877 |
| Unnamed 30 Degree Scope | No Camera | 1.424591739 | 0.712536023 | 0.987861877 |
| P.O.C. 30 Degree Scope | Zoomed In | 0.690654702 | 0.342216187 | 0.99962506 |
| P.O.C. 30 Degree Scope | Zoomed Out | 1.385714286 | −0.115714286 | 0.999362719 |
| P.O.C. 30 Degree Scope | No Camera | 1.448640084 | 0.143543702 | 0.992908484 |
| KARL STORZ 0 Degree Scope | Zoomed In | 0.650879968 | 0.115592248 | 0.999823319 |
| KARL STORZ 0 Degree Scope | Zoomed Out | 1.282195333 | 0.160328436 | 0.999677717 |
| KARL STORZ 0 Degree Scope | No Camera | 1.38677686 | 0.009256198 | 0.987097382 |

A number of size constraints also exist for the size of range-finding spot 602. For example, range-finding spot 602 should never be larger than camera FOV 600, and usually smaller, which puts a limit on slope (i.e., NA) of range-finding spot 602 relative to camera FOV 600. In fact, at large X, the final spot size is given by $m_1/m_2$, which should be approximately 40-50% in the example above. Finally, the range-finding spot size is relatively constrained to be a small fraction of the objective lens diameter, with the smaller starting diameters increasing the sensitivity in the example shown in FIGS. 6A-6B whereby the diameter of range-finding spot 602 grows.

The choice of the $b_1$, $m_1$, $b_2$, $m_2$, s, z, Epsilon, and Zeta parameters requires modeling such that the effect of each variable can be measured and final choices made. In various embodiments, any or all of the following steps can be used to determine these design parameters:

1.) Select objective lens diameter $b_2$ based on scope size. The larger $b_2$, the larger the sensitivity of measurements at large object distances.
2.) Select the FOV divergence (akin to NA) of the objective lens based on user requirement specifications. As mentioned above, a typical clinical scope has a FOV divergence (NA≈0.7), so $m_2$=1.4 should be selected in that case. The NA needs to be clinically useful, but the smaller the better in terms of sensitivity to object distance.
3.) Select the range-finding spot size slope $m_1$ to be the desired fraction of the FOV. In the example above, $m_1$ should be ≈40-50% of $m_2$. Note, however, that this choice depends on the final choice of objective lens diameter.
4.) Select the range-finding fiber diameter $b_1$ to be as small as possible relative to $b_2$. Although this limits the amount of light that enters the fiber, it also increases sensitivity when the diameter of the range-finding spot changes.
5.) Separation distance z is usually constrained by the physical scope size, but separation s, and angles Epsilon and Zeta, may be chosen to maximize sensitivity to large object distances.

The following is an example of how spot size changes with object distance X from 1 cm to 10 cm. It does not take into account vertical movement of the spot using angle Epsilon, but does show how quickly the spot size converges.

Spot: $m_1$=0.5 (NA=0.25), $b_1$ (fiber diameter=initial spot size)=0.01 cm (100 μm)

Camera: $m_2$=1.25 (NA=0.625), $b_2$ (objective lens diameter)=0.25 cm (2.5 mm)

Figure 6E:
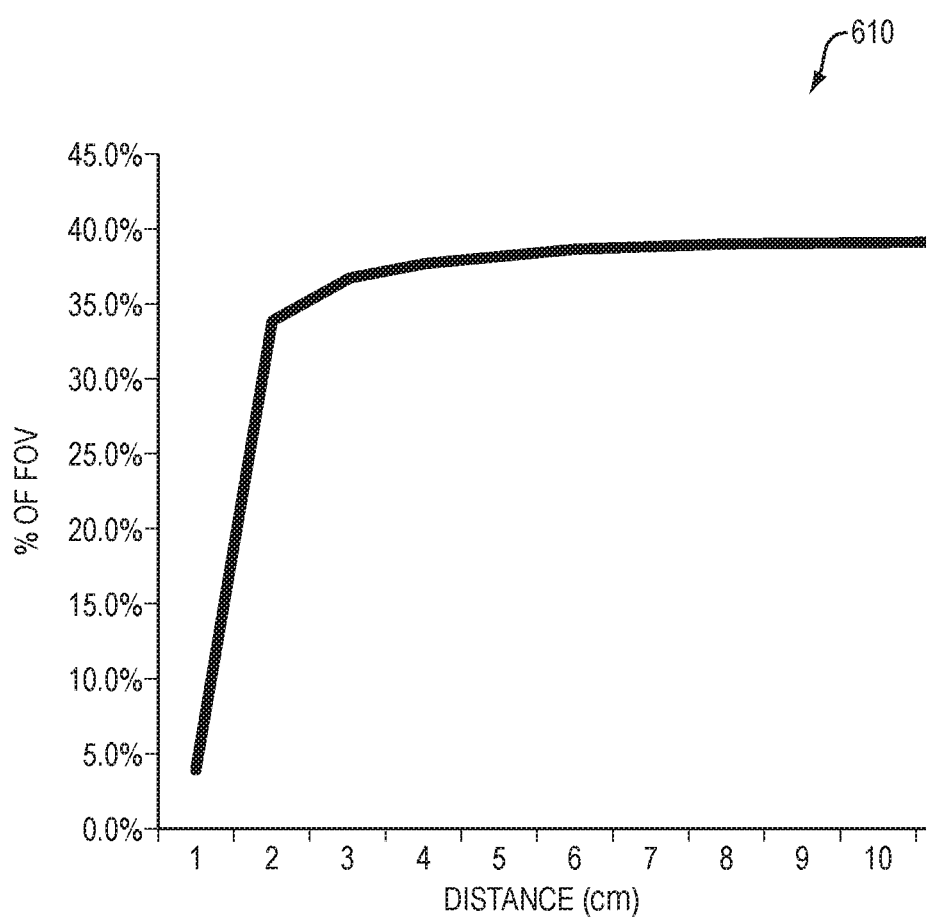

FIG. 6E illustrates a plot 610 of object range versus spot size percentage of camera field of view, based on the computation of spot size for different object distances. From plot 610, it can be seen that just by using spot diameter alone, there is high sensitivity and dynamic range (almost 10 fold, albeit non-linear) between 0-4 cm, but from 4-10 cm, spot size alone will not suffice to determine the range. By judicious choice of starting size, position, and growth of the spot (i.e., selection of s, z, Epsilon, and Zeta), there will be nearly as many pixels in the camera field of view available for movement of the spot diagonally as there are for spot growth, thus giving us approximately 10-fold sensitivity for distances from 4-10 cm. Of note, in the example above, the final spot size was selected to be 40% of the total FOV, so that there can be significant diagonal movement of the spot to improve long distance measurements.

Figure 7:
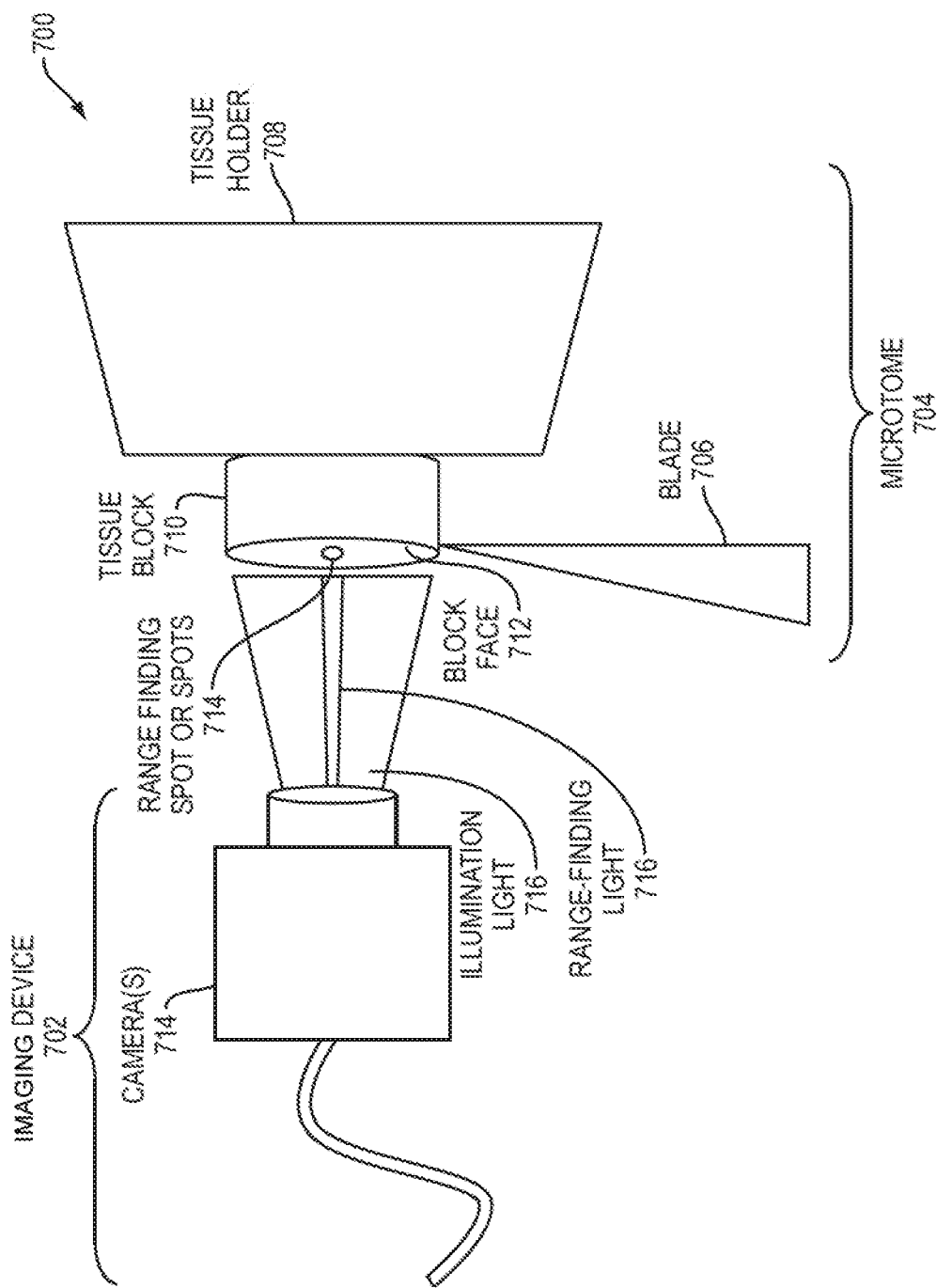
FIG. 7 illustrates an example imaging system for a microtome.

FIG. 7 illustrates an example of imaging a block of tissue using the imaging techniques herein, according to various embodiments. As noted above, the techniques herein may be used for in vivo imaging, such as in the case of open surgical, endoscopic, or laparoscopic imaging. In further embodiments, the techniques herein can also be used to perform ex vivo imaging of organic tissue that has been excised from a host organism. One such example is illustrated in system 700 shown, which generally includes an imaging device/system 702 and a microtome 704.

In general, a microtome is a specialized tool used to slice a collected sample into very fine slices. Typically, this is performed using one or more blades. However, some microtomes may also use a laser as the cutting mechanism for the sample. During operation, the sample and/or the cutting mechanism may move relative to one another, to remove a very thin slice of the sample from a sample block. For example, as shown, consider a tissue block 710 of organic tissue that has been mounted to a tissue holder 708 within a microtome. To obtain a slice of tissue material from tissue block 710, a blade 706 may cut through tissue block 710 along an axis that is substantially parallel to the block face 712 of tissue block 710. As would be appreciated, this may be achieved by maintaining the tissue holder 708 at a static location and moving blade 706 through the tissue block 710, holding blade 706 at a static location and moving tissue holder 708 and tissue block 710 across blade 706, or a combination thereof. The width of the resulting tissue slice will be a function of the distance of the blade 706 relative to the surface of black face 712.

In some embodiments, the microtome 704 may also be a specialized form of microtome known as a cryomicrotome (for small samples) or a cryomacrotome (for large samples). Collectively, the term 'cryotome' may refer to either such device. Cryomicrotomes typically operate in a manner similar to that of other microtomes (i.e., to obtain slices of sample material), but are adapted for specific use in slicing frozen samples. Notably, the inner chamber of a cryotome may maintain an inner temperature that is much lower than that of the ambient room temperature, to aid in maintaining the frozen state of the sample. Typically, the sample (e.g., tissue block 710) is first prepared by suspending and freezing the sample within an optimal cutting temperature (OCT) compound.

During operation, imaging device 702 may operate camera(s) 714, to image the block face 712 of tissue block 710, in accordance with the techniques herein. Notably, imaging device 702 may be configured to capture both visible and near-infrared fluorescence images of tissue block 710 and output a combined image to an electronic display coupled to imaging device 702. For example, suitable systems for imaging device 702 may include the LAB-FLARE® (FLuorescence-Assisted Resection and Exploration) imaging systems available from Curadel LLC, Marlborough, Mass. In other words, during preparation, tissue block 710 may be infused with a dye/fluorophore, either while still in vivo or ex vivo, thereby allowing imaging device 702 to capture fluorescence images of the contrast agent within tissue block 710. For example, in the case of a cryotome, tissue block 710 may be infused with the agent, prior to freezing within the OCT compound. A heated glass window can be used to prevent condensation from interfering with imaging by the camera.

Imaging of block face 712 by imaging device 702 may be performed repeatedly, as follows. First, the topmost layer of tissue block 710 may be removed using blade 706. Next, imaging device 702 may be operated to capture both color and fluorescence/near infrared images of the exposed block face 712. In some cases, imaging device 702 may include a visible light source that works in conjunction with its color camera(s) 714. In other cases, ambient room lighting may be used as the light source. Similarly, the infrared camera(s) 714 of imaging device 702 may operate in conjunction with one or more infrared light sources of imaging device 702, to capture the fluorescence images and obtain detailed images of the fluorescent dye suspended within tissue block 710.

In turn, a controller of imaging device 702 may combine the color and fluorescence images (e.g., as an overlay image, etc.), and provide the display information to an electronic display. In some embodiments, the captured images across different iterations of slicing and imaging may be combined to form a three dimensional (3-D) representation of the detected fluorescent dye within tissue block 710.

In further embodiments, imaging device 702 may be used to image the resulting slices of tissue block 710 in lieu of, or in combination with, that of the images of block face 712. For example, imaging device 702 may be operated in conjunction with a microscope, to capture images of histologic slices obtained through the operation of microtome 704 on tissue block 710. The range-finding light could also be on the tissue block 710, blade 706, or tissue holder 708, in further embodiments. If blade 706 is stationary, the biggest risk is when tissue holder 708 comes into contact with it, so the range should be monitored at this time. If blade 706 is moving, then that is when it should be monitored by the range finder.

To implement the techniques herein for purposes of block face imaging, imaging system/device 702 may emit range-finding light 716 onto the surface of block face 712 and/or the surface of tissue holder 708, to produce one or more range-finding spots 714. Note that the more spots 714, the more accurate the range finding, which is of particular use when there are multiple "levels" being imaged. Likewise, imaging device 702 may emit illumination light 716 onto block face 712, to illuminate the full portion of block face 712 that is being imaged. In turn, the controller of imaging device 702 may asses the captured image data from block face 712 to determine a distance between spot(s) 714 and the edge of the captured image(s) and translate this distance into a distance between the end of imaging device 702 and block face 712. While typically of significant benefit in the case of in vivo imaging (e.g., endoscopic, laparoscopic, open surgical, etc.), the techniques herein may also be of some use in ex vivo systems, as well. Notably, the high intensity of the illumination at certain distances may, in some cases, cause there to be some temperature differences in the tissue block that are deemed undesirable. And, irreparable damage to the blade can be prevented by knowing the distance from the blade 706 to the tissue holder 708 and avoiding collision.

Various camera configurations and modes of operation were also assessed. In particular, range-finding capabilities using the techniques herein were extended to 2-sensor imagers (e.g., visible and NIR) and to 3-sensor imagers (e.g., visible, NIR1, NIR2) and utilized on many different modes. In general, a single range-finding spot wavelength is required for 2-sensor imagers and two different range-finding spot wavelengths are required for 3-sensor imagers. The latter permits the real-time operation of either NIR channel in range-finding mode. When range-finding is used in addition to the maximum number of NIR channels of the camera, a loss of frame rate is inevitable, although it is relatively small as shown in Table 2 below:

TABLE 2

| Number of Camera Sensors | Number of Range-Finding Wavelengths Needed | Mode of Operation | Max per Sensor Frame Rate | Final Image Frame Rate |
| --- | --- | --- | --- | --- |
| 2 (Color, NIR1/2) | 1 (808 nm) | 700 nm without RF | 30 fps (33 msec) | 30 fps (33 msec) |
| | | 700 nm with RF (808 nm) | | 15 fps (67 msec) |
| | | 800 nm without RF | | 30 fps (33 msec) |
| | | 800 nm with RF (808 nm) | | 15 fps (67 msec) |
| | | 700 nm and 800 nm without RF | | 15 fps (67 msec) |
| | | 700 nm and 800 nm with RF (808 nm) | | 10 fps (100 msec) |

TABLE 2-continued

| Number of Camera Sensors | Number of Range-Finding Wavelengths Needed | Mode of Operation | Max per Sensor Frame Rate | Final Image Frame Rate |
|---|---|---|---|---|
| 3 (Color, NIR1, NIR2) | 2 (730 nm; 808 nm) | 700 nm without RF | 30 fps (33 msec) | 30 fps (33 msec) |
| | | 700 nm with RF (808 nm) | | 30 fps (33 msec) |
| | | 800 nm without RF | | 30 fps (33 msec) |
| | | 800 nm with RF (730 nm) | | 30 fps (33 msec) |
| | | 700 nm and 800 nm without RF | | 30 fps (33 msec) |
| | | 700 nm and 800 nm with RF (808 nm) | | 15 fps (67 msec) |

Because the fluorescence imaging components do most of the work, and image processing will be used to derive an object distance measurement, the only three things needed to equip a fluorescence imaging scope with range-finding capabilities may be a range-finding light source, a filter to ensure that the range-finding illumination light stays within its desired camera channel, and a range-finding light delivery fiber.

There are two options for range-finding light generation, laser diodes and LEDs. To reduce the overall complexity of a scope-based imager, the range-finding light source may be mounted inside the scope handle, rather than inside its associated cart. Although both 3.8 mm diameter laser diodes or 3-3.5 mm square LEDs will fit well, LEDs are preferable because of their low cost and ease of driving. During prototyping, the following LEDs were found suitable for range-finding in terms of power, wavelength, and size, as shown in Table 3 below:

TABLE 3

| Wavelength | Overall Size (WDH) | Approx. Die Size | Max Drive Current | Optical Power | Manufacturer | Model # |
|---|---|---|---|---|---|---|
| 730 ± 15 nm (80° FWHM) | 3 × 3 × 2.4 mm | 1 × 1 mm | 1000 mA | 300 mW | Osram | GF CS8PM2.24 |
| 810 nm (30° FWHM | 3.5 × 3.5 × 1.6 mm | 1 mm D | 500 mA | 390 mW | Osram | SFH 4786S |

However, laser diodes from LDX having a die size of ≈50 µm and an overall size of 5.6 mm diameter were also found to be capable of implementing the techniques herein.

Note that for the two-sensor imager prototype, the range-finding wavelength of 810 nm was selected because it is poorly seen by the human eye and will not affect the quality of surgical imaging. Even when a 700 nm range-finding spot was tested, an LED wavelength as far red as possible was selected, again to limit the perception of the spot by the human eye.

Of course, given the high divergence angles of the LEDs and the very small (≈0.1 mm diameter) range-finding fibers, only a very small fraction of the total optical power is transmitted. Laser diodes, even without a focusing lens, would definitely be more efficient in launching light into the fiber, but the cost is significant.

A filter between the range-finding light source and fiber is essential for removing out of band light. For example, most LEDs and laser diodes have red tails, so when a 730 nm source is used, the tail could easily extend into the emission (camera) band of the 800 nm channel. To prevent this, a small (typically 3±0.1 mm square×1±0.1 mm thick) interference filter was placed between the light source and fiber. The filters were chosen to be identical to the camera emission filters, which provides a wide range, to capture as much light as possible while eliminating the possibility that range-finding light from one channel will leak into the other. The filters listed in Table 4 below were found to be suitable during testing:

TABLE 4

| Filter Name | Transmitted Wavelengths | Size | Material |
|---|---|---|---|
| ET781LP | >781 nm | 3 × 3 × 1 (±0.1) mm | UVFS |
| ET710/50 m | 685-735 nm | 3 × 3 × 1 (±0.1) mm | UVFS |

The two options for fibers are single core quartz or glass fibers (core/clad/optional plastic coating) or fiber bundles. Glass fibers are readily available at a variety of NA from 0.25 NA to 0.66 NA, and in a wide variety of diameters from 30 µm to 500 µm codes. Special order glass fibers of 30 µm or 50 µm are available at NA 0.12 and 0.87. Fused silica (quartz) fibers are available at 0.12, 0.22, and 0.26 NA from Fiberguide Industries™, which also have various coating including autoclave-compatible polyimide. Glass fibers, in particular, will be extremely cost-effective because they can be ground and polished as a batch then used as single fibers. Their only disadvantage is that they are not readily available with a plastic coating, although this should not be needed. However, it was found that the use of a bundle of fibers should generally be avoided, in most cases (but not all), because of the small size of $b_1$ in the modeling above and the lack of space in the smaller scopes. The main downside to small fibers, and especially small fibers with low NA, is that light collection from the source is extremely limited.

By way of example, if a FOV divergence equivalent to 0.7 NA is selected for the objective lens, and a 40% final spot size is desired, the NA of the range-finding fiber should be 0.40*0.7=0.28. To use a conventional glass fiber of 0.25, the scope NA can be reduced to 0.625 and achieve the proper ratio.

A significant amount of time was devoted during prototyping to devise a driving and coupling system for the range-finding LED(s). In one prototype, a very small LED printed circuit board (PCB) was soldered vertically to the main scope PCB such that the LEDs are at 90° and facing the barrel of the scope. Then, to each LED was added a housing into which the filter has been epoxied with custom black UV cure. Preferably, the housing itself will be black, in order to absorb all light not entering the fiber, but needs to compatible with autoclaving (steam sterilization) and easy to manufacture. In terms of materials evaluated during testing, PEEK plastic meets all of the above criteria and is available as a convenient ¼" diameter black rod starting material (e.g., McMaster 7707T11).

Figure 8A:
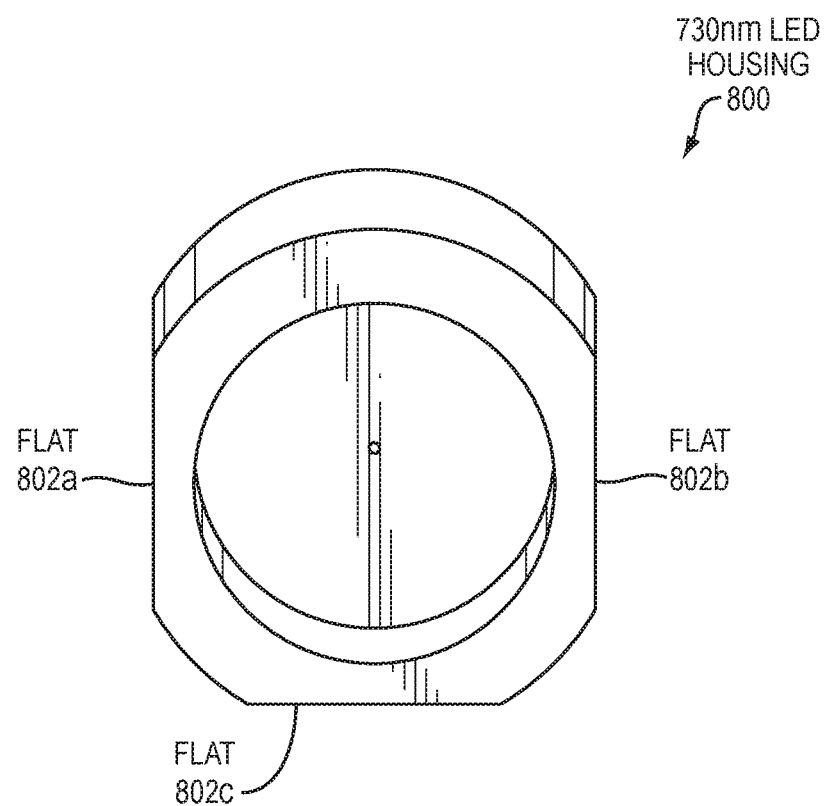
FIGS. 8A-8F illustrate examples of light emitting diode (LED) mounting.
Figure 8B:
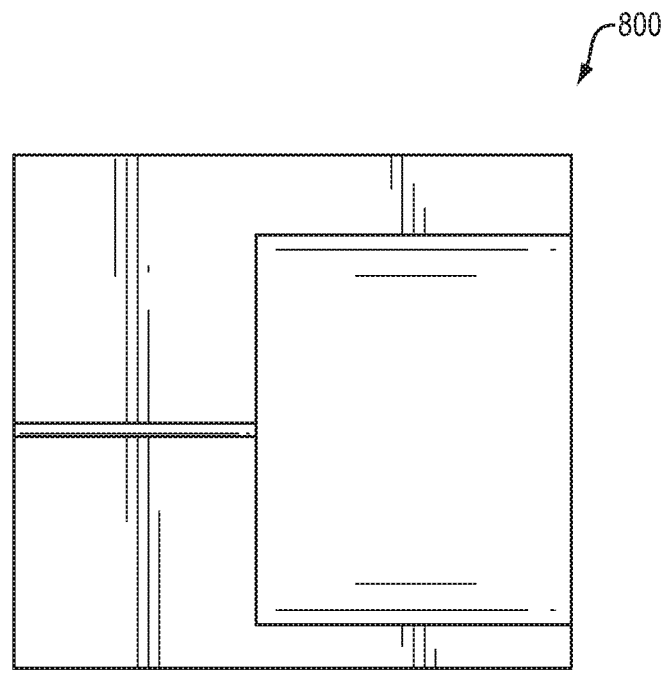
Figure 8C:
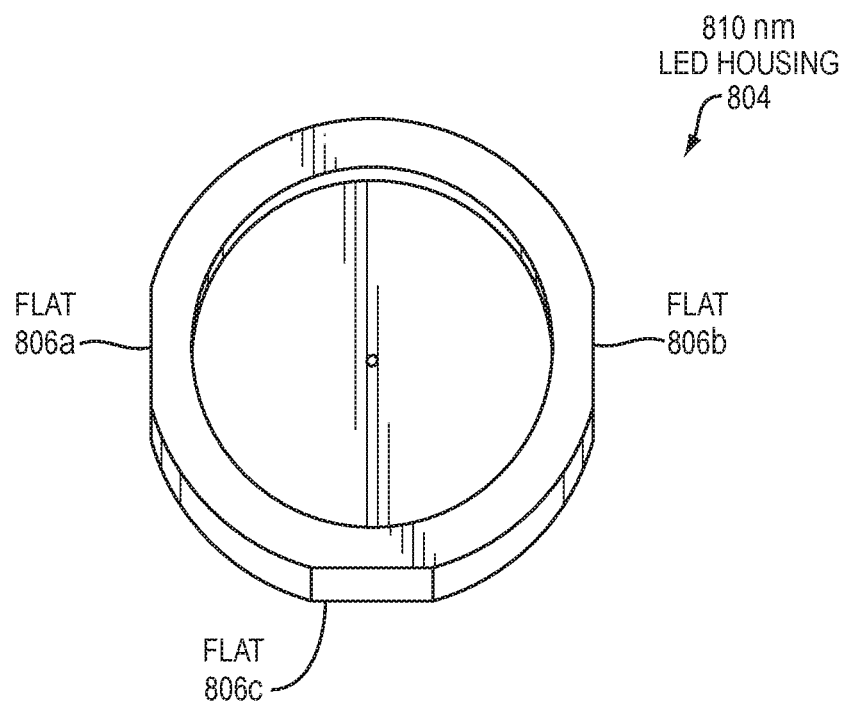
Figure 8D:
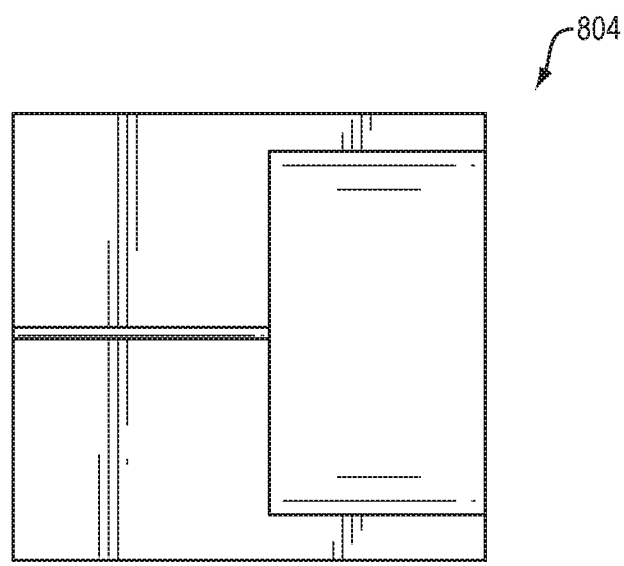

FIGS. 8A-8B respectively illustrate example rear and side/cross-sectional views of a housing 800 for a 730 nm LED. Similarly, FIGS. 8C-8D respectively illustrate example rear and side/cross-sectional views of a housing 806 for an 810 nm LED. During prototyping, simple flats (e.g., flats 802 and 806) were added to the sides of housings 800 and 804, allowing two different LED holders to be placed closer together. In addition, a flat bottomed LED housing also allows it to be leveled with the main PCB and permit rapid ultraviolet (UV) curing in place. Finally, a custom black UV curing epoxy was developed that bonds materials like PEEK and PCBs well while preventing the epoxy from being a light pipe. Two different housings 800 and 804, one for a 730 nm LED and one for an 810 nm LED, were purposely developed to minimize the distance between fiber and LED (with filter in between), while also permitting population of one LED, or both, as needed, with both fitting well side by side.

Figure 8E:
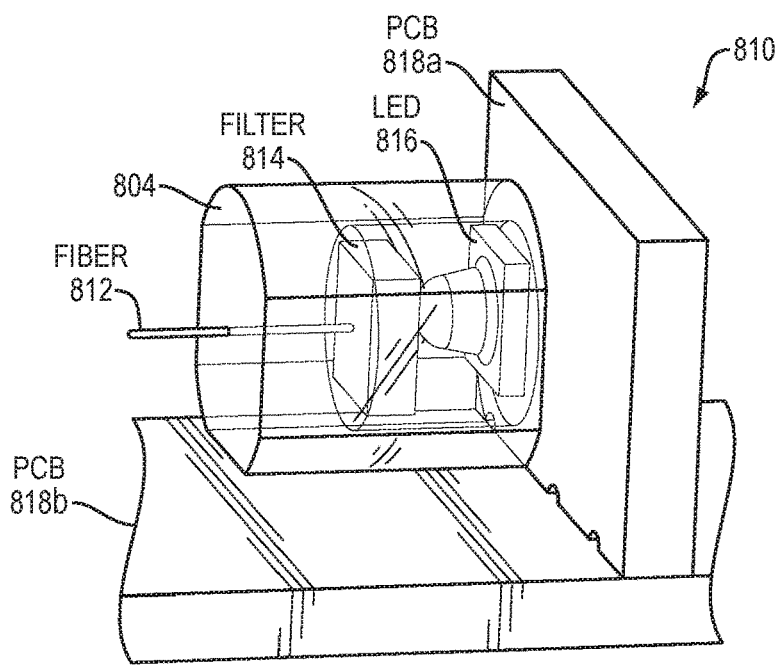
Figure 8F:
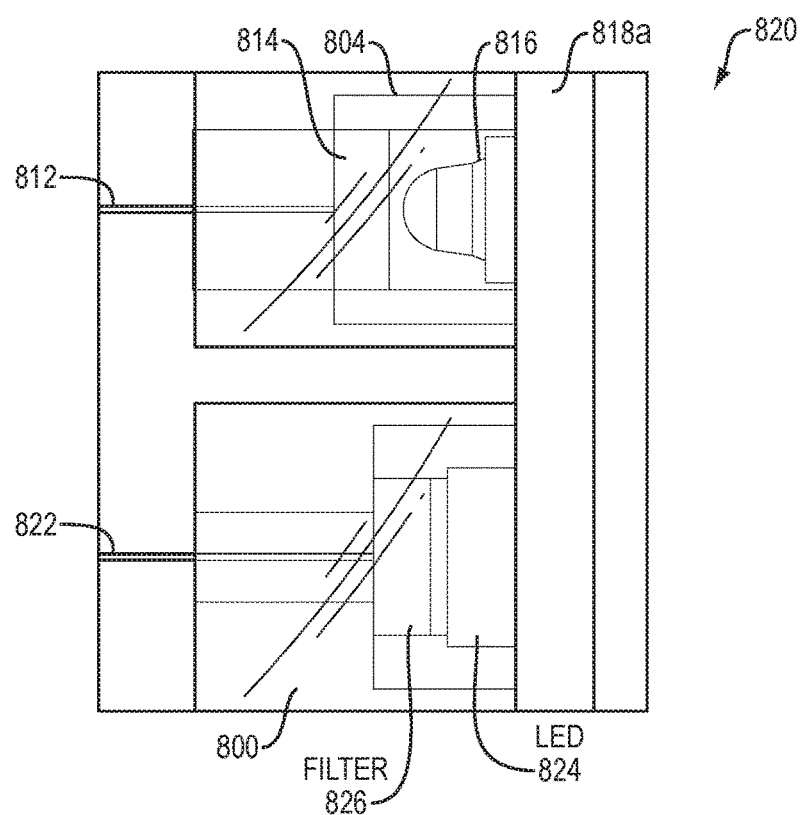

FIGS. 8E-8F illustrate examples of the final LED range-finding assemblies mounted to the main scope PCB. More specifically, FIG. 8E illustrates a range-finding LED assembly 810 for use with a 2-sensor camera, whereas FIG. 8F illustrates a range-finding LED assembly 820 for use with a 3-sensor camera. As shown in FIG. 8E, the PCB 818a for a single 810 nm LED 816 can be mounted vertically to the main scope PCB 818b and housed within LED housing 804. A range-finding illumination fiber 812 may extend through housing 804, separated from LED 816 by a filter 814.

FIG. 8F illustrates a top view of range-finding LED assembly 820 for use with 3-sensor imagers. As noted above, a 3-sensor imager may capture visible light images, as well as NIR images at two different wavelengths (e.g., 730 nm and 810 nm). In such a case, assembly 810 can be modified to form assembly 820 that supports the two NIR LEDs 816 (e.g., 810 nm) and 824 (e.g., 730 nm). As shown, LEDs 816 and 824 can be mounted side by side on the LED PCB 818a, which is mounted vertically on the main PCB 818b. Thanks to the flats of their respective housings 804 and 800, LEDs 816 and 824 can also be placed in close proximity to one another. Similar to LED 816, LED 824 may be located within a housing 800 through which a fiber 822 extends. A filter 826 can also be located within housing 800, thereby separating LED 824 from fiber 822.

To mount fibers 812 and/or 822 within a scope, the frame that holds the CMOS sensors, filters, objective lens, and RF fiber(s) must be manufactured with high precision, especially given the sensitivity of the range-finding sub-system to the parameter values of z, s, Epsilon, and Zeta. Microelectromechanical systems (MEMS) technology would be ideal for this, but presently only works well for Z-heights under 0.5-1 mm. However, as MEMS technology advances, this may become the preferred manufacturing approach. In another embodiment, the frames can be manufactured by MEMS in layers and then attached. Alternatively in yet another embodiment, a frame could be constructed using laser micromachining.

Regardless of the final manufacturing process chosen, each individual scope with range-finding capabilities may need to be calibrated. This process may entail measuring the entire range of spot size, shape, quality, and location within the FOV, at all desired object distances X. In further embodiments, this calibration can also be automated using a linear stage and the resulting values retained in the onboard memory (e.g., EEPROM).

While the techniques herein are described primarily with respect to using NIR spots for purposes of performing the range-finding, other wavelengths can be used, in further embodiments. Notably, so long as the range finding wavelength does not conflict with the wavelength of the illumination used to image the field of view of the camera (e.g., visible or NIR), other range-finding wavelengths can also be used. For example, non-visible light, such as ultraviolet (UV) or infrared (IR) light, may also be suitable for projecting range finding spots onto the subject undergoing imaging, in further embodiments.

Figure 9:
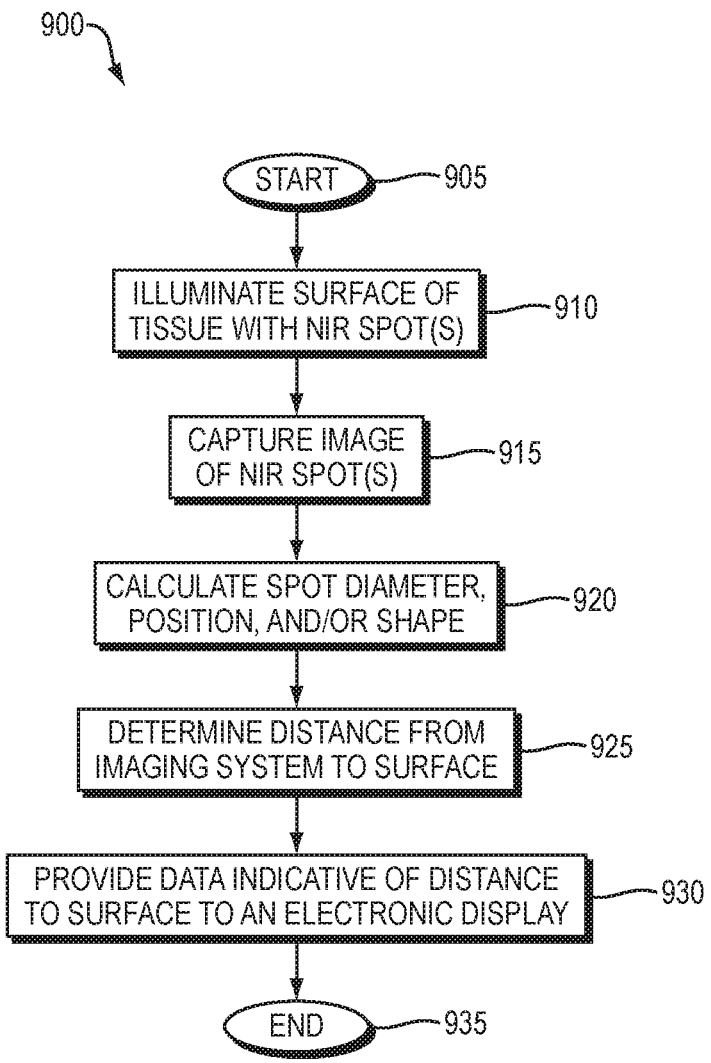
FIG. 9 illustrates an example simplified procedure for performing range-finding in an imaging system.

FIG. 9 illustrates an example simplified procedure 900 for performing range-finding in an imaging system, in accordance with one or more embodiments described herein. For example, a non-generic, specifically configured imaging system may perform procedure 900 by executing stored instructions (e.g., process 248), to implement the range-finding techniques herein. Procedure 900 may start at step 905 and may continue on to step 910 where, as described in greater detail above, the imaging system may illuminate a surface of tissue with one or more spots of near-infrared (NIR) light within a field of view of a camera of the imaging system.

At step 915, as detailed above, the imaging system may capture an image of the one or more spots of NIR light within the field of view of the camera of the imaging system. As would be appreciated, a higher number of spots may provide for greater range-finding precision, especially in the case of a non-uniform topology of the tissue being imaged. However, the techniques herein have also been found to work with only a single range-finding spot.

At step 920, the imaging system may calculate, for each of the one or more spots of NIR light in the captured image, a spot diameter, spot position, and/or spot shape in the captured image, as described in greater detail above. As noted above, the spot diameter alone has been shown to be suitable to perform a lookup of the range, when the range is between 0-4 cm. However, at farther distances, the position of the spot (e.g., vertical movement) can also be taken into account, to discern the distance between the imaging system and the surface of the tissue or other object being imaged. In cases in which the exact number of pixels is known for the camera field of view, the spot diameter and position can be represented in terms of these pixels, in some embodiments.

At step 925, as detailed above, the imaging system may determine a distance between the imaging system and the surface of tissue, based on the calculated spot diameter, spot position, and/or spot shape of the one or more spots of NIR light in the captured image. In various embodiments, calibration of the imaging system prior to deployment can be performed to populate a calibration lookup table that the imaging system can then use to look up the range to the object being imaged using the techniques highlighted above. The spot shape can also be used for purposes of determining the distance between the imaging system and the surface of the tissue, in some embodiments. Notably, the shape of a range finding spot may indicate a non-uniform topology of the surface of tissue, which can then be used to estimate the distance to the closest portions of the tissue. Note that the imaging system may perform the range-finding in conjunction with fluorescence imaging (e.g., by masking the range-finding spots from display to the user) or in an alternating manner (e.g., by alternating between fluorescence imaging and range-finding). In further embodiments, it may also be possible to determine the distance based on the captured light intensities either in lieu of the spot analysis or in addition thereto. Notably, even when assessment of only the intensities would be unreliable for purposes of range-finding, due to absorption and/or scatter effects on the surface being imaged, this information can still be used for purposes of improving range-finding accuracy.

At step 930, the imaging system may provide data indicative of the determined distance between the imaging system and the surface of tissue to an electronic display, as described in greater detail above. In some cases, the determined distance can also be leveraged for surgical navigation, such as by combining the determined distance with data from an accelerometer, gyroscope, or the like. Procedure 900 then ends at step 935.

It should be noted that while certain steps within procedure 900 may be optional as described above, the steps shown in FIG. 9 are merely examples for illustration, and certain other steps may be included or excluded as desired. Further, while a particular order of the steps is shown, this ordering is merely illustrative, and any suitable arrangement of the steps may be utilized without departing from the scope of the embodiments herein.

It will be appreciated that the above functionality is merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention. Accordingly, the techniques herein provide a range-finding mechanism that determines or approximates the distance between an optical imaging system and a surface of a subject being imaged. In some aspects, the techniques provide for the use of range-finding spots in an imaging system that are invisible to the user, either by hiding the imaging window used to measure the particular wavelength of the range-finding spots or by constantly alternating between imaging and range-finding with the optical imaging device, but only displaying the imaging information. In doing so, this creates a situation whereby the imaging "workflow" is not interrupted by the range-finding functions.

As will be appreciated, the above examples are intended only for the understanding of certain aspects of the techniques herein and are not limiting in nature. While the techniques are described primarily with respect to a particular device or system, the disclosed processes may be executed by other devices according to further implementations. For example, while the techniques herein are described primarily with respect to medical and research imaging, the techniques herein are not limited as such and can be adapted for use in other industries, as well. Further, while the techniques herein are described particularly in the context of NIR fluorescence imaging systems, the range-finding techniques herein are not limited as such and can be applied within any number of different types of optical imaging systems.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method comprising:
   illuminating, by an imaging system, a surface of tissue with one or more spots of near-infrared (NIR) light within a field of view of a camera of the imaging system;
   capturing, by the imaging system, an image of the one or more spots of NIR light within the field of view of the camera of the imaging system;
   calculating, by the imaging system and for each of the one or more spots of NIR light in the captured image, a spot diameter, spot position, or spot shape in the captured image;
   determining, by the imaging system, a distance between the imaging system and the surface of tissue, based on the calculated spot diameter, spot position, or spot shape of the one or more spots of NIR light in the captured image, wherein the one or more spots of NIR light move diagonally in the field of view as a tip of the imaging system moves from a first position to a second position that is closer to the surface; and
   providing, by the imaging system, data indicative of the determined distance between the imaging system and the surface of tissue to an electronic display.

2. The method of claim 1, wherein the illuminating the surface of tissue with the one or more spots of NIR light within the field of view of the camera of the imaging system is carried out using an NIR light source providing corresponding one or more range finding NIR light beams with a respective fixed angular orientation that intersects an optical axis of the camera a distance downstream of the camera, wherein calculating the distance between the imaging system and the surface of tissue comprises:

using the calculated spot diameter, spot position, or spot shape of the one or more spots of NIR light in the captured image to perform a lookup of the distance between the imaging system and the surface of tissue from a calibration lookup table of the imaging system.

3. The method of claim 1, wherein the illuminating the surface of tissue with one or more spots of NIR light within a field of view of a camera of the imaging system comprises:
concurrently illuminating the surface of tissue with a plurality of spots of NIR light as the one or more spots within the field of view of the camera with an NIR light source providing corresponding range finding NIR light beams with respective fixed angular orientations that intersect an optical axis of the camera a distance downstream of the camera, and, wherein the capturing, by the imaging system, of the image of the one or more spots of NIR light within the field of view of the camera of the imaging system captures a series of images whereby the spot diameter, spot position, or spot shape of the plurality of spots of NIR light in the series of captured images is used to determine the distance between the imaging system and the surface of tissue.

4. The method of claim 1, wherein the illuminating the surface of tissue with one or more spots of NIR light within a field of view of a camera of the imaging system comprises:
illuminating the surface of tissue with the one or more spots of NIR light via at least one range finding optical fiber of the imaging system, wherein the at least one range finding optical fiber defines a range finding beam axis having a fixed angular orientation that intersects an optical axis of the field of view of the camera at a location that is downstream of the camera, wherein the at least one range finding optical fiber is separated from the optical axis by a distance Z in a first axis and a distance S in a second axis, and is angularly offset in the first axis relative to the optical axis by angle Epsilon and angularly offset in the second axis relative to the optical axis by angle Zeta whereby the angle Epsilon determines sensitivity to large object distances and the angle Zeta determines a left/right position of the one or more spots at large distances, and wherein the separation distances Z, S and the angles Epsilon and Zeta are configured to force simultaneous horizontal and vertical movements of the one or more range finding spots within the field of view of the camera in response to movement of the tip of the imaging system.

5. The method of claim 4, wherein the imaging system comprises an endoscope or laparoscope through which the optical fiber extends, wherein the distance between the imaging system and the surface of tissue is a distance between a tip of the endoscope or laparoscope and the surface of the tissue.

6. The method of claim 5, further comprising:
performing, via a working channel of the endoscope or laparoscope, a procedure to the tissue comprising one of: biopsy, resection, lavage, or injection, using the determined distance between the imaging system and the surface of the tissue.

7. The method of claim 1, further comprising:
performing, by the imaging device, fluorescence imaging of the tissue by capturing visible light and NIR images of the tissue; and
providing, by the imaging device, an image that combines the visible light and NIR images of the tissue to the electronic display.

8. The method of claim 7, further comprising:
alternating, by the imaging device, between performance of the fluorescence imaging and capturing of images of the one or more spots of NIR light within the field of view of the camera of the imaging system.

9. The method of claim 1, further comprising:
using, by the imaging system, the determined distance between the imaging system and the surface of tissue with accelerometer or gyroscope data, to perform three dimensional surgical navigation.

10. An imaging system comprising:
a visible light camera having an optical axis and a field of view;
a near-infrared (NIR) light source configured to emit at least one range finding beam, each emitted range finding beam of the at least one range finding beam having a respective fixed orientation relative to the optical axis;
an NIR camera; and
a controller coupled to the NIR light source, visible light camera, and NIR camera, the controller comprising a processor configured to execute a process and a memory configured to store the process, the process when executed configured to:
direct the NIR light source to emit the at least one range finding beam with each range finding beam of the at least one range finding beam having a respective fixed orientation relative to the optical axis to illuminate, a surface of tissue with one or more spots of NIR light within a field of view of the visible light camera;
capture, using the NIR camera, an image of the one or more spots of NIR light within the field of view of the visible light camera;
calculate, for each of the one or more spots of NIR light in the captured image, a spot diameter, spot position, or spot shape in the captured image;
determine a distance between the imaging system and the surface of tissue, based on the calculated spot diameter, spot position, or spot shape of the one or more spots of NIR light in the captured image; and
provide data indicative of the determined distance between the imaging system and the surface of tissue to an electronic display,
wherein the NIR light source comprises at least one range finding optical fiber that is separated from the optical axis by a distance Z in a first axis and a distance S in a second axis, and that is angularly offset in the first axis relative to the optical axis by angle Epsilon and angularly offset in the second axis relative to the optical axis by angle Zeta whereby the angle Epsilon determines sensitivity to large object distances and the angle Zeta determines a left/right position of the one or more spots at large distances, and wherein the separation distances Z, S and the angles Epsilon and Zeta are configured to force simultaneous horizontal and vertical movements of the one or more range finding spots within the field of view of the camera in response to movement of a distal end of the imaging system.

11. The imaging system of claim 10, wherein the one or more spots of NIR light moves/move diagonally in the field of view as the visible light camera moves from a first position to a second position that is closer to the surface, wherein the one or more spots of NIR light has/have a spot size that changes as the visible light camera moves from the first position to the second position, and wherein the imaging system calculates the distance between the imaging system and the surface of tissue by:

using the calculated spot diameter, spot position, or spot shape of the one or more spots of NIR light in the captured image to perform a lookup of the distance between the imaging system and the surface of tissue from a calibration lookup table in the memory of the controller.

12. The imaging system of claim 10, wherein the imaging system provides the NIR light source as two or more NIR light sources, and wherein the imaging system illuminates the surface of tissue with one or more spots of NIR light within the field of view of the visible light camera by:
illuminating the surface of tissue with two or more spots of NIR light from the two or more NIR light sources within the field of view of the visible light camera.

13. The imaging system of claim 10, wherein the at least one range finding optical fiber is arranged with respect to a lens of the camera to have a first slope m1 of spot divergence, wherein the lens has a second slope m2 of lens divergence, and wherein m1 is in a range of 40-50% of m2.

14. The imaging system of claim 10, wherein the at least one range finding optical fiber is held in a fixed orientation in a channel of a shaft of the imaging system to define a fixed range-finding axis of a corresponding one of the at least one range-finding beam, wherein the optical axis is defined by a lens of the visible light camera providing the field of view of the visible light camera, and wherein the range-finding axis intersects the optical axis at a distance downstream of the lens.

15. The imaging system of claim 10, wherein the imaging system comprises an endoscope or laparoscope through which the at least one range finding optical fiber extends, and wherein the distance between the imaging system and the surface of tissue is a distance between a tip of the endoscope or laparoscope and the surface of the tissue.

16. The imaging system of claim 10, wherein the process when executed is further configured to:
perform fluorescence imaging of the tissue by capturing visible light via the visible light camera and NIR images of the tissue via the NIR camera; and
provide an image that combines the visible light and NIR images of the tissue to the electronic display.

17. The imaging system of claim 16, wherein the process when executed is further configured to:
alternate between performance of the fluorescence imaging and capturing of images of the one or more spots of NIR light within the field of view of the visible light camera.

18. The imaging system of claim 10, wherein the process when executed is further configured to:
use the determined distance between the imaging system and the surface of tissue with accelerometer or gyroscope data, to perform three dimensional surgical navigation.

19. A microtome comprising:
a tissue holder configured to retain a block of tissue;
a blade configured to move across the retained block of tissue to produce a slice of tissue sample from the block of tissue; and
an imaging system configured to:
perform fluorescence imaging on the block of tissue, and
perform range-finding on at least one of: the block of tissue, the tissue holder, or the blade,
wherein the imaging system comprises a visible light camera and an NIR light source, wherein the imaging system is configured to define a range-finding NIR light beam with a fixed orientation that generates an NIR light spot, wherein the NIR light spot is configured to move diagonally inside a field of view of a visible light camera from a first position at a first distance to a second position at a second distance that is closer to the block of tissue, and wherein the NIR light spot reduces in size from the first position to the second position.

20. The microtome of claim 19, wherein the range-finding light beam is parallel to an optical axis of the visible light camera.

21. The method of claim 1, wherein the field of view is divided into quadrants with the optical axis extending through a center of the field of view, and wherein the one or more spots reside in one or more of the quadrants and move and reduce in size within the field of view as the camera moves closer to the surface.

22. The method of claim 1, wherein the one or more spots of NIR light have a spot size that changes in response to a distance of the tip from the surface whereby the spot size changes in size more at closer distances to the surface and the one or more spots move diagonally a greater amount at longer distances over 4 cm from the surface to thereby provide dynamic range and sensitivity.

23. The method of claim 22, wherein the one or more spots have a maximal spot size when the camera is 10 cm from the surface that is about 40%-50% of a total surface area of the field of view.

* * * * *